US012691229B1

(12) United States Patent
Hee-Hanson et al.

(10) Patent No.: US 12,691,229 B1
(45) Date of Patent: Jul. 28, 2026

(54) MEDICAMENT DELIVERY DEVICE

(71) Applicant: Genzyme Corporation, Cambridge, MA (US)

(72) Inventors: Alexander Hee-Hanson, Melbourn (GB); Thomas Lever, Melbourn (GB); Michael Parrott, Melbourn (GB); Robert Wilson, Melbourn (GB); Haiming Wu, Cambridge, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 19/064,300

(22) Filed: Feb. 26, 2025

(51) Int. Cl.
*A61M 5/315* (2006.01)

(52) U.S. Cl.
CPC ...... *A61M 5/3158* (2013.01); *A61M 5/31536* (2013.01)

(58) Field of Classification Search
CPC ........... A61M 5/3158; A61M 5/31536; A61M 5/3202; A61M 5/3213; A61M 5/3204; A61M 5/50; A61M 5/3219; A61M 2005/3217; A61M 2005/312; A61M 2205/273; A61M 5/178; A61M 5/20; A61M 5/24; A61M 5/28; A61M 5/31; A61M 5/31578; A61M 5/321; A61M 5/3216; A61M 2005/3103; A61M 2005/3107; A61M 2005/3109; A61M 2005/3118; A61M 2005/3117; A61M 2005/3215; A61M 2005/3254
See application file for complete search history.

(56) References Cited

U.S. PATENT DOCUMENTS 2,522,961 A     9/1950   William
2,633,267 A     3/1953   Lebus
(Continued)

FOREIGN PATENT DOCUMENTS

DE        3921747 A1     1/1991
EP        3501577 A1     6/2019
(Continued)

OTHER PUBLICATIONS

Hamers-Casterman et al., "Naturally occurring antibodies devoid of light chains," Nature, Jun. 3, 1993, 363(6428):446-448.
(Continued)

*Primary Examiner* — Kevin C Sirmons
*Assistant Examiner* — Alexandra Lalonde
(74) *Attorney, Agent, or Firm* — Fish & Richardson P.C.

(57) ABSTRACT

A medicament delivery device is described. The device includes a body having proximal and distal ends defining a longitudinal direction; a needle for injecting medicament into a user and configured to be arranged in an injecting position in which the needle protrudes from the distal end of the body; a cap moveable along the longitudinal direction to be arrangeable in a capped position in which the cap conceals the distal end of the body, and an uncapped position in which at least a portion of the cap is spaced apart from the distal end; and a blocking element. When the cap is in the uncapped position, the blocking element is arrangeable in a first state in which movement of the cap from the uncapped position into the capped position is permitted, and a second state in which movement of the cap from the uncapped position into the capped position is prevented.

10 Claims, 11 Drawing Sheets

(56) References Cited

U.S. PATENT DOCUMENTS

| | | | |
|---|---|---|---|
| 3,886,513 | A | 5/1975 | Smith et al. |
| 4,801,295 | A | 1/1989 | Spencer |
| 5,045,062 | A | 9/1991 | Henson |
| 5,176,275 | A | 1/1993 | Bowie |
| 5,328,484 | A | 7/1994 | Somers et al. |
| 5,396,051 | A | 3/1995 | Kuhn et al. |
| 5,478,316 | A | 12/1995 | Bitdinger et al. |
| 5,505,324 | A | 4/1996 | Danico |
| 5,505,706 | A | 4/1996 | Maus et al. |
| 5,536,917 | A | 7/1996 | Suppelsa et al. |
| 5,622,274 | A | 4/1997 | Bright |
| 5,738,658 | A | 4/1998 | Maus et al. |
| 5,984,899 | A | 11/1999 | D'Alessio et al. |
| 6,080,461 | A | 6/2000 | Wozniak et al. |
| 6,394,985 | B1 | 5/2002 | Lin |
| 7,762,981 | B2 | 7/2010 | Dacquay et al. |
| 7,887,506 | B1 | 2/2011 | Smolyarov et al. |
| 7,918,824 | B2 | 4/2011 | Bishop et al. |
| 8,133,198 | B2 | 3/2012 | Neer |
| 8,409,138 | B2 | 4/2013 | James et al. |
| 8,734,394 | B2 | 5/2014 | Adams et al. |
| 9,044,553 | B2 | 6/2015 | James et al. |
| 9,402,957 | B2 | 8/2016 | Adams et al. |
| 9,474,780 | B2 | 10/2016 | Bokvist et al. |
| 9,872,961 | B2 | 1/2018 | Fourt et al. |
| 10,118,001 | B2 | 11/2018 | Fourt et al. |
| 10,314,981 | B2 | 6/2019 | Sampson et al. |
| 10,350,362 | B2 | 7/2019 | Dennis, Jr. et al. |
| 10,363,377 | B2 | 7/2019 | Atterbury et al. |
| 11,103,657 | B2 | 8/2021 | Brown et al. |
| 11,298,462 | B2 | 4/2022 | Atterbury et al. |
| 11,331,432 | B2 | 5/2022 | Holmqvist et al. |
| 11,357,820 | B2 | 6/2022 | Corvari et al. |
| 11,369,751 | B2 | 6/2022 | Ruan et al. |
| 11,452,821 | B2 | 9/2022 | LaFever et al. |
| 2002/0055712 | A1 | 5/2002 | Neracher |
| 2004/0039336 | A1 | 2/2004 | Amark et al. |
| 2005/0101919 | A1 | 5/2005 | Brunnberg |
| 2005/0273061 | A1 | 12/2005 | Hommann et al. |
| 2006/0224124 | A1 | 10/2006 | Scherer |
| 2007/0270777 | A1 | 11/2007 | Dacquay et al. |
| 2008/0097311 | A1 | 4/2008 | Dacquay et al. |
| 2008/0097390 | A1 | 4/2008 | Dacquay et al. |
| 2008/0269692 | A1 | 10/2008 | James et al. |
| 2009/0036868 | A1 | 2/2009 | Pinedjian et al. |
| 2009/0281496 | A1 | 11/2009 | Matusch |
| 2010/0211005 | A1 | 8/2010 | Edwards et al. |
| 2011/0054414 | A1 | 3/2011 | Shang et al. |
| 2011/0144594 | A1 | 6/2011 | Sund et al. |
| 2011/0202011 | A1 | 8/2011 | Wozencroft |
| 2011/0319813 | A1 | 12/2011 | Kamen et al. |
| 2013/0237921 | A1 | 9/2013 | Lannan et al. |
| 2013/0267897 | A1 | 10/2013 | Kemp et al. |
| 2014/0236076 | A1 | 8/2014 | Marshall et al. |
| 2014/0249483 | A1 | 9/2014 | Kiilerich et al. |
| 2014/0263156 | A1 | 9/2014 | Newsom et al. |
| 2014/0276637 | A1 | 9/2014 | Massey, Jr. |
| 2015/0246180 | A1 | 9/2015 | Fenlon et al. |
| 2015/0273162 | A1 | 10/2015 | Holmqvist |
| 2016/0001015 | A1 | 1/2016 | Kucuk et al. |
| 2016/0354555 | A1 | 12/2016 | Gibson et al. |
| 2016/0367763 | A1 | 12/2016 | Tschirren et al. |
| 2017/0215699 | A1 | 8/2017 | Ouyang et al. |
| 2017/0216526 | A1 | 8/2017 | Brereton et al. |
| 2017/0224929 | A1 | 8/2017 | Sampson et al. |
| 2017/0246403 | A1 | 8/2017 | Cowe et al. |
| 2017/0361034 | A1 | 12/2017 | Scheller et al. |
| 2018/0036492 | A1* | 2/2018 | Schader .............. A61M 5/2033 |
| 2018/0250471 | A1 | 9/2018 | Grimoldby et al. |
| 2018/0339114 | A1 | 11/2018 | Wendland et al. |
| 2019/0030249 | A1 | 1/2019 | Gonzalez et al. |
| 2019/0192785 | A1 | 6/2019 | Wendland et al. |
| 2019/0366000 | A1 | 12/2019 | Cowe et al. |
| 2020/0114041 | A1 | 4/2020 | Alas et al. |
| 2020/0316314 | A1 | 10/2020 | Buri et al. |
| 2021/0077732 | A1 | 3/2021 | Egelhofer |
| 2021/0196900 | A1 | 7/2021 | Apply et al. |
| 2021/0402102 | A1 | 12/2021 | Timmis et al. |
| 2022/0015429 | A1 | 1/2022 | Brown et al. |
| 2022/0176042 | A1 | 6/2022 | Belisle |
| 2022/0395640 | A1 | 12/2022 | Schwartzentruber |
| 2023/0001099 | A1 | 1/2023 | Dunn |
| 2023/0238105 | A1 | 7/2023 | Schneider et al. |
| 2023/0347074 | A1 | 11/2023 | Gavin |
| 2024/0009397 | A1 | 1/2024 | In et al. |

FOREIGN PATENT DOCUMENTS

| | | | |
|---|---|---|---|
| WO | WO 2002/047746 | A1 | 6/2002 |
| WO | WO 2004/058820 | A2 | 7/2004 |
| WO | WO 2004/068820 | A2 | 8/2004 |
| WO | WO 2005/018629 | A1 | 3/2005 |
| WO | WO 2006/003388 | A2 | 1/2006 |
| WO | WO 2006/030220 | A1 | 3/2006 |
| WO | WO 2011/109205 | A2 | 9/2011 |
| WO | WO 2016/081238 | A1 | 5/2016 |
| WO | WO 2019/074788 | A1 | 4/2019 |
| WO | WO 2020/190529 | A1 | 9/2020 |

OTHER PUBLICATIONS

Holt et al., "Domain antibodies: proteins for therapy," Trends in Biotechnology, Nov. 2003, 21(11):484-490.

Muyldermans, "Single domain camel antibodies: current status," Reviews in Molecular Biotechnology, Jun. 2001, 74(4):277-302.

Needle-based injection systems for medical use requirements and test methods, Part 1: Needle injection systems, ISO 11608-1:2014(E), Third Edition, Switzerland, ISO, Dec. 15, 2014, pp. 1-13.

Ward et al., "Binding activities of a repertoire of single immuno-globulin variable domains secreted from *Escherichia coli*," Nature, Oct. 1, 1989, 341(6242):544-546.

International Search Report and Written Opinion in International Appln. No. PCT/US2026/016258, mailed on May 20, 2026, 12 pages.

* cited by examiner

MEDICAMENT DELIVERY DEVICE

TECHNICAL FIELD

The present disclosure relates to a medicament delivery device.

BACKGROUND

Medicament delivery devices, such as auto-injectors, are known in the art for dispensing medicament to an injection site of a patient. Some medicament delivery devices comprise a cap configured to conceal an end of the device, for example to conceal a needle thereof. In order to prepare such a medicament delivery device for medicament delivery, the cap may be removed. It is possible to re-cap some devices, i.e. to reapply the cap into a capped position, pre or post use of the device. In some cases, re-capping a device pre-use can result in a bent needle which may lead to injection pain, wasted drug, and/or a wet injection site.

SUMMARY

A first aspect of this disclosure provides a medicament delivery device, comprising: a body having proximal and distal ends defining a longitudinal direction; a needle for injecting medicament into a user and configured to be arranged in an injecting position in which the needle protrudes from the distal end of the body; a cap moveable along the longitudinal direction to be arrangeable in a capped position in which the cap conceals the distal end of the body, and an uncapped position in which at least a portion of the cap is spaced apart from the distal end of the body; and a blocking element, wherein when the cap is in the uncapped position, the blocking element is arrangeable in: a first state in which movement of the cap from the uncapped position into the capped position is permitted, and a second state in which movement of the cap from the uncapped position into the capped position is prevented; wherein moving the cap from the uncapped position into the capped position, and/or moving the cap from the capped position into the uncapped position, causes the blocking element to be arranged in the second state.

In some embodiments, moving the cap from the uncapped position into the capped position, and/or moving the cap from the capped position into the uncapped position, causes the blocking element to move from the first state into the second state.

In some embodiments, moving the cap from the uncapped position into the capped position causes the blocking element to be arranged in the second state.

In some embodiments, moving the cap from the capped position into the uncapped position causes the blocking element to be arranged in the second state.

In some embodiments, moving the cap from the uncapped position into the capped position and then subsequently moving the cap from the capped position into the uncapped position causes the blocking element to be arranged in the second state.

In some embodiments, moving the cap from the capped position into the uncapped position causes the blocking element to move from the first state into the second state.

In some embodiments, moving the cap from the capped position into the uncapped position when the cap has already previously been in the uncapped position causes the blocking element to be arranged in the second state.

That is, capping the device, or uncapping the device, or both capping and then subsequently uncapping the device, with the cap, causes the blocking element to be placed into the second state. Thus, if the device has previously been capped, i.e. if the cap has previously been in the capped position at any time, then the blocking element is automatically caused to be arranged in the second state upon removal of the cap, such that any subsequent movement of the cap from the uncapped position into the capped position is prevented, such that the cap is blocked from being placed in the capped position again, hence re-capping is not permitted.

In some embodiments, moving the cap from the uncapped position into the capped position comprises moving the cap along the longitudinal direction to bring the cap into contact with the distal end of the body.

In some embodiments, moving the cap from the uncapped position into the capped position further comprises rotating the cap relative to the body.

In some embodiments, moving the cap from the uncapped position into the capped position comprises moving the cap along the longitudinal direction and then rotating the cap relative to the body.

In some embodiments, moving the cap from the uncapped position into the capped position comprises rotating the cap relative to the body and then moving the cap along the longitudinal direction.

In some embodiments, when the cap is in the capped position, the cap is coupled to the body, and when the cap is in the uncapped position, the cap is decoupled from the body.

In some embodiments, the cap is configured to be removable from the body.

In some embodiments, the body is generally elongate and cylindrical.

In some embodiments, the cap comprises a generally circular cross section.

In some embodiments, the cap comprises plastic.

In some embodiments, the blocking element is configured to limit the range of motion of the cap along the longitudinal direction, for example in a direction towards the distal end of the body.

In some embodiments, the blocking element is configured to not obstruct movement of the cap from the capped position into the uncapped position.

In some embodiments, the blocking element is configured to not limit the range of motion of the cap along the longitudinal direction in a direction away from the distal end of the body.

In some embodiments, the cap is arrangeable in a first initial uncapped position in which the cap has not previously been in the capped position, and a second subsequent uncapped position in which the cap has previously been in the capped position; wherein when the cap is in the first initial uncapped position, the blocking element is configured to be in the first state, and when the cap is in the second subsequent uncapped position, the blocking element is configured to be in the second state.

In some embodiments, the medicament delivery device further comprises a needle shield assembly receivable inside the body and configured to circumscribe at least a portion of the needle, wherein the cap is configured to receive the needle shield assembly to couple the cap to the needle shield assembly.

In some embodiments, the cap comprises a receiving portion for receiving the needle shield assembly.

In some embodiments, the cap is configured to receive the needle shield assembly in an interference fit.

In some embodiments, the cap comprises a body portion configured to be held by a user and the receiving portion is arranged to protrude from the body portion.

In some embodiments, the receiving portion is arranged to protrude into the body along the longitudinal direction when the cap is coupled to the body.

In some embodiments, the cap comprises a contact surface and when the cap is in the capped position, the contact surface is configured to contact and abut the distal end of the body.

In some embodiments, the contact surface is generally flat in a plane that is generally normal to the longitudinal direction.

In some embodiments, the needle shield assembly comprises a needle cover configured to circumscribe at least a portion of the needle, and a cap insert configured to receive the needle cover and to be received by the cap.

In some embodiments, the needle cover is generally cylindrical and hollow.

In some embodiments, the cap insert is configured to receive the needle cover.

In some embodiments, the cap is configured to receive the cap insert.

In some embodiments, the cap is configured to receive the cap insert in an interference fit.

In some embodiments, the cap insert is configured to receive the needle cover in an interference fit.

In some embodiments, the cap insert is configured to be moved along the longitudinal direction to couple the cap insert to the needle cover.

In some embodiments, the cap is configured to be moved along the longitudinal direction to couple the cap to the cap insert.

In some embodiments, moving the cap from a first initial uncapped position in which the cap has not previously been in the capped position, into the capped position, causes the cap to be coupled to the needle shield assembly.

In some embodiments, the needle shield assembly is configured to be movable relative to the body along the longitudinal direction, such that when the needle shield assembly is coupled to the cap, the needle shield assembly and the cap are configured to be together movable relative to the body along the longitudinal direction.

In some embodiments, when the cap is in the uncapped position and the needle shield assembly is not coupled to the cap, the blocking element is configured to be in the first state; and wherein when the cap is in the uncapped position and the needle shield assembly is coupled to the cap, the blocking element is configured to be in the second state.

In some embodiments, when the cap is in the capped position, the cap is configured to form a snap fit connection with the body to couple the cap to the body.

In some embodiments, the snap fit connection is a one way snap fit connection.

In some embodiments, moving the cap from a first initial uncapped position in which the cap has not previously been in the capped position, into the capped position, causes the cap and the body to be arranged in the snap fit connection.

In some embodiments, rotating the cap relative to the body about the longitudinal direction causes the cap and the body to be arranged in the snap fit connection when the cap is in the capped position.

In some embodiments, the medicament delivery device comprises a plurality of blocking elements.

In some embodiments, the plurality of blocking elements are angularly spaced apart from one another about a central longitudinal axis of the body.

In some embodiments, the plurality of blocking elements are equally spaced apart from one another about a central longitudinal axis of the body.

In some embodiments, the cap comprises the blocking element, or the blocking element is coupled to or integrally formed with the body.

In some embodiments, the cap comprises the blocking element.

In some embodiments, the cap comprises the blocking element, and the medicament delivery device further comprises an engagement element arranged to protrude inside the body along a radially inwards direction that is generally normal to the longitudinal direction, wherein when the blocking element of the cap is in the second state, the blocking element of the cap is configured to abut the engagement element to prevent movement of the cap along the longitudinal direction from the uncapped position into the capped position.

In some embodiments, the medicament delivery device comprises a plurality of engagement elements.

In some embodiments, each of the plurality of engagement elements is configured to engage with a respective one of the plurality of blocking elements.

In some embodiments, the plurality of engagement elements are angularly spaced apart from one another about a central longitudinal axis of the body.

In some embodiments, the plurality of blocking elements are equally spaced apart from one another about a central longitudinal axis of the cap.

In some embodiments, the engagement element comprises a chamfered surface angled relative to the longitudinal direction and configured to facilitate movement between the engagement element and the blocking element.

In some embodiments, the engagement element comprises a collar arranged inside the body.

In some embodiments, the collar is generally annular.

In some embodiments, the collar is configured to rotate relative to the body.

In some embodiments, the collar comprises a first circumferential portion comprising the chamfered surface and a second circumferential portion which does not comprise the chamfered surface.

In some embodiments, movement of the cap along the longitudinal direction is configured to cause the collar to rotate relative to the body.

In some embodiments, the cap is configured to be moved from a first initial uncapped position wherein the cap has not previously been in the capped position, into the capped position, when the first circumferential portion of the collar is circumferentially aligned with the blocking element of the cap; and movement of the cap along the longitudinal direction towards the distal end causes the collar to rotate relative to the cap such that the second circumferential portion of the collar is circumferentially aligned with the blocking element of the cap when the cap is in the capped position.

In some embodiments, when the first circumferential portion of the cap is circumferentially aligned with the blocking element, movement of the cap from the uncapped position into the capped position is permitted, and when the second circumferential portion of the cap is circumferentially aligned with the blocking element, movement of the cap from the uncapped position into the capped position is prevented.

In some embodiments, rotation of the collar into a position such that the second circumferential portion is circumferentially aligned with the blocking element causes the arm to flex relative to the longitudinal direction.

In some embodiments, the cap comprises an arm arranged to protrude generally along the longitudinal direction towards the distal end of the body, wherein a free end of the arm comprises the blocking element.

In some embodiments, relative to a central longitudinal axis of the body along a radial direction that is generally normal to the longitudinal direction, the arm comprises an outermost surface and the engagement element comprises an innermost surface.

In some embodiments, the outermost surface of the arm is configured to overlap with the innermost surface of the engagement element when the blocking element is in the second state.

In some embodiments, the innermost surface of the engagement element is arranged to be radially closer to a central longitudinal axis of the body than the outermost surface of the arm.

In some embodiments, in order to move the arm past the engagement element along the longitudinal direction towards the proximal end of the body, the arm is configured to be deflected or displaced to cause the outermost surface of the arm to be temporarily arranged radially inwards relative to the innermost surface of the engagement element, with respect to a central longitudinal axis of the body.

In some embodiments, the arm comprises a fixed end and a free end.

In some embodiments, the fixed end is coupled to or integrally formed with a main body portion of the cap, and the free end is configured to protrude from the body portion of the cap and into the body of the medicament delivery device.

In some embodiments, the arm comprises a first portion comprising the fixed end and a second portion comprising the free end, wherein the second portion has a larger cross-sectional area than the first portion.

In some embodiments, the second portion is wider and/or thicker than the first portion.

In some embodiments, the second portion is at least approximately half the length of the first portion.

In some embodiments, the second portion is approximately equal in length to the first portion.

In some embodiments, the second portion is greater in length than the first portion.

In some embodiments, the cross-sectional area of the second portion is at least 25% larger than the cross-sectional area of the first portion, for example at least 30%, 40%, 50%, 60%, 70%, 80%, 90% or 100% larger.

In some embodiments, the cross-sectional area of the second portion is at least twice as large as the cross-sectional area of the first portion.

In some embodiments, the cap comprises a plurality of arms each comprising a blocking element at its respective free end.

In some embodiments, the plurality of arms are angularly spaced apart from one another about a central longitudinal axis of the cap.

In some embodiments, the plurality of arms are equally spaced apart from one another about a central longitudinal axis of the cap.

In some embodiments, the cap comprises two arms which are diametrically opposed from one another.

In some embodiments, when the cap is in a first initial uncapped position in which the cap has not previously been in the capped position, the arm is configured to be displaced from the engagement element such that the blocking element is spaced apart from the engagement element such that movement of the cap along the longitudinal direction from the uncapped position into the capped position is permitted; and wherein when the cap is in a second subsequent uncapped position in which the cap has previously been in the capped position, the blocking element of the arm is configured to abut the engagement element to prevent movement of the cap along the longitudinal direction from the uncapped position into the capped position.

In some embodiments, when the cap is in a first initial uncapped position in which the cap has not previously been in the capped position, the arm is displaceable from the engagement element such that the blocking element can be spaced apart from the engagement element such that movement of the cap along the longitudinal direction from the uncapped position into the uncapped position is permitted.

In some embodiments, when the cap is in a second subsequent uncapped position in which the cap has previously been in the capped position, the arm is not displaceable from the engagement element, such that the blocking element is configured to be aligned with, to abut with, to contact, to interfere with, to contact, and/or to engage with the engagement element, such that movement of the cap along the longitudinal direction from the uncapped position into the capped position is prevented.

In some embodiments, the arm is configured to flex relative to the body, such that the arm may be arranged in a flexed state in which the arm is orientated to be angled relative to the longitudinal direction, and in an unflexed state in which the arm is orientated to be generally parallel to the longitudinal direction.

In some embodiments, when the arm is in the flexed state the blocking element is spaced apart from the engagement element.

In some embodiments, when the arm is in the unflexed state the blocking element is configured to be aligned with the engagement element.

In some embodiments, along a radial direction that is generally normal to the longitudinal direction, when the arm is in the flexed state the blocking element is spaced apart from the engagement element and when the arm is in the unflexed state the blocking element is configured to be aligned with the engagement element.

In some embodiments, when the arm is in the flexed state the blocking element is configured to be disengaged from the engagement element, and when the arm is in the unflexed state the blocking element is configured to be engageable with the engagement element.

In some embodiments, moving the cap along the longitudinal direction from a first initial uncapped position in which the cap has not previously been in the capped position, into the capped position, causes the arm to move from the unflexed state, into the flexed state during said movement, and then back into the unflexed state upon the completion of such movement.

In some embodiments, the arm is configured to move into the flexed state in order to facilitate movement of the cap from the uncapped position into the capped position.

In some embodiments, the arm is configured to flex relative to the body to facilitate the formation of a snap fit connection with the engagement element.

In some embodiments, moving the cap from the capped position into the uncapped position causes the arm to move from the unflexed state into the flexed state and then back into the unflexed state.

In some embodiments, when the cap is in the uncapped position and the blocking element is arranged in the second state, the arm is in the unflexed state.

In some embodiments, the arm is biased towards the position in which the arm is configured to abut the engagement element.

In some embodiments, the arm is biased towards the unflexed state.

In some embodiments, the arm comprises a chamfered surface angled relative to the longitudinal direction, wherein the chamfered surface is configured to facilitate movement between the arm and the engagement element.

In some embodiments, the arm comprises a blocking surface arranged at a free end of the arm.

In some embodiments, the blocking surface is generally flat in a plane generally normal to the longitudinal direction, wherein the blocking surface is configured to abut and engage with the body clip interface, to block movement of the cap along the longitudinal direction from the uncapped position into the capped position.

In some embodiments, the blocking surface is arranged to be generally opposite to the chamfered surface.

In some embodiments, the arm is configured to flex or deflect relative to the engagement element to displace the arm from the engagement element such that the blocking element can be spaced apart from the engagement element.

In some embodiments, the cap and the engagement element are configured to be rotatable relative to one another between a disengaged position in which the blocking element is spaced apart from the engagement element and an engaged position in which the blocking element abuts the engagement element.

In some embodiments, the cap is configured to be rotated relative to the engagement element to move between the disengaged and engaged positions.

In some embodiments, the engagement element is configured to be rotated relative to the cap to move between the disengaged and engaged positions.

In some embodiments, the engagement element is integrally formed with the body.

In some embodiments, the engagement element is coupled to the body.

In some embodiments, the engagement element is arranged inside the body and protrudes from an inner surface of the body towards a central longitudinal axis of the body.

In some embodiments, the blocking element and/or the engagement element comprises a chamfered surface inclined relative to the longitudinal direction, to facilitate movement between the blocking element and the engagement element.

In some embodiments, the chamfered surface is generally linear and straight.

In some embodiments, at least a portion of the chamfered surface is a curved surface.

In some embodiments, the blocking element comprises a chamfered surface.

In some embodiments, the engagement element comprises a chamfered surface.

In some embodiments, the blocking element and/or the engagement element comprises a curved surface to facilitate movement between the blocking element and the engagement element.

In some embodiments, the blocking element is coupled to or integrally formed with the body and wherein at least a portion of the blocking element is configured to move in a radial direction that is generally normal to the longitudinal direction, such that when the blocking element is in the first state, said at least a portion of the blocking element is arranged in a radially outward position, and such that when the blocking element is in the second state, said at least a portion of the blocking element is arranged in a radially inward position that is radially inward relative to the radially outward position, relative to a central longitudinal axis of the medicament delivery device; and wherein the blocking element is biased towards the radially inward position.

In some embodiments, the movement in the radial direction comprises a linear translational movement and/or a pivoting or deflecting or flexing movement.

In some embodiments, the blocking element comprises plastic.

In some embodiments, the blocking element is generally block shaped, or generally wedge shaped.

In some embodiments, the blocking element is generally block shaped and comprises a chamfered surface angled relative to the longitudinal axis.

In some embodiments, the chamfered surface is inclined relative to the longitudinal direction and is configured to slope inwards towards a central longitudinal axis of the body in a direction from the proximal end towards the distal end.

In some embodiments, the medicament delivery device comprises a plurality of blocking elements, which may be angularly spaced apart from one another, for example equally spaced apart, about a central longitudinal axis of the body.

In some embodiments, the blocking element is generally annular and may extend around substantially the entire circumference of an inner surface of the body.

In some embodiments, the blocking element is configured to move relative to the pre-filled syringe, the needle cover, the cap insert and the cap along the radial direction.

In some embodiments, the blocking element is configured to move along the radial direction in order to selectively block or otherwise impede movement of the cap along the longitudinal direction, in order to prevent re-capping.

In some embodiments, the blocking element is configured to move along the radial direction in order to selectively block or otherwise impede movement of the needle cover and the cap insert when the needle cover and the cap insert are coupled to the cap after the cap has already been placed in the capped position.

In some embodiments, the blocking element is coupled to the body via a biasing means.

In some embodiments, the biasing means comprises a spring.

In some embodiments, the biasing means comprises a compression spring, wherein when the blocking element is in the first state, the spring is in a compressed, stressed state, and when the blocking element is in the second state, the spring is in an uncompressed, unstressed, natural state.

In some embodiments, the blocking element is configured to be fixed relative to the body along the axial direction.

In some embodiments, the blocking element comprises a leg comprising a fixed end coupled to or integrally formed with the body and a free end configured to be movable relative to the fixed end.

In some embodiments, the free end of the leg is configured to move relative to the fixed end of the leg in a radial direction that is generally normal to the longitudinal direction.

In some embodiments, the leg is configured to flex between a flexed state and an unflexed state.

In some embodiments, the free end of the leg is configured to flex or pivot relative to the fixed end of the leg.

In some embodiments, when the blocking element is in the first state, the leg is configured to be in the flexed state, and when the blocking element is in the second state, the leg is configured to be in the unflexed state.

In some embodiments, the leg comprises a main portion extending between the fixed end and the free end.

In some embodiments, when the leg is in the flexed state, the main portion is arranged to be angled relative to the longitudinal direction, and when the leg is in the unflexed state, the main portion is arranged to be generally parallel to the longitudinal direction.

In some embodiments, the leg comprises plastic.

In some embodiments, the blocking element comprises a flexible arm.

In some embodiments, the blocking element comprises an annulus or ring.

In some embodiments, the blocking element comprises an annulus oriented to be generally normal to the longitudinal direction such that it circumscribes a central longitudinal axis of the body.

In some embodiments, the annulus is configured to selectively become larger and/or smaller in diameter, for example by being formed of a stretchable or elastic material, and/or by comprising one or more folds.

In some embodiments, the medicament delivery device contains a medicament.

In some embodiments, the medicament delivery device comprises a pre-filled syringe arranged inside the body.

In some embodiments, the pre-filled syringe comprises the needle.

In some embodiments, the pre-filled syringe contains a medicament.

In some embodiments, the pre-filled syringe is configured to be movable along the longitudinal direction relative to and inside the body.

According to another aspect of the present disclosure there is provided a method of manufacturing or assembling a medicament delivery device, wherein the medicament delivery device is defined in claim 1. Further optional features of the medicament delivery device are described and/or contemplated here.

According to another aspect of the present disclosure there is provided a method of manufacturing or assembling a medicament delivery device, wherein the medicament delivery device has the features of any of the medicament delivery devices described and/or contemplated herein.

BRIEF DESCRIPTION OF THE DRAWINGS

Embodiments will now be described, by way of example only, with reference to the accompanying drawings, in which.

DETAILED DESCRIPTION

Figures 1A, 1B:
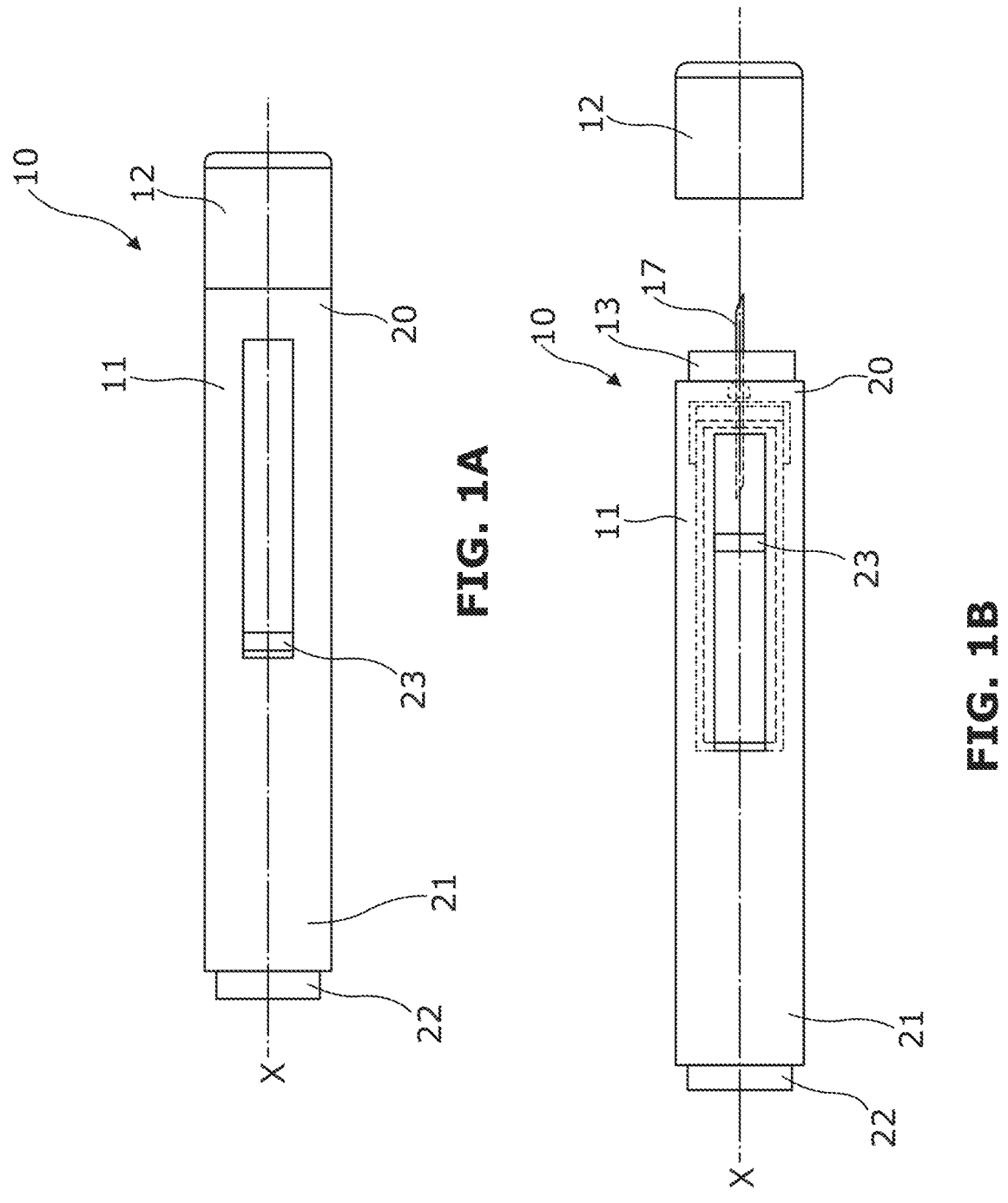
FIG. 1A shows a schematic view of a medicament delivery device with a cap attached.
FIG. 1B shows a schematic view of the medicament delivery device of FIG. 1A with the cap removed.

A drug delivery device (also referred to as an injection device), as described herein, may be configured to inject a medicament into a subject such as a human or animal. For example, delivery could be sub-cutaneous, intra-muscular, or intravenous. Such a device could be operated by a user, who may or may not be the subject. In examples where the user is not the subject, the user may be a care-giver such as a nurse or physician. The device can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a subject's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge. The dispensing mechanism provides one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

The medicament delivery device can include various types of safety syringe, pen-injector, or auto-injector. The device can include a cartridge-based system that requires piercing a sealed ampule before use.

Distal movement of the actuation member may cause automatic dispensing of the medicament from the device and/or distal movement of the actuation member may cause the distal movement of the needle from a needle pre-use position to a needle injection position. The dispensing mechanism may be configured to dispense medicament from the needle when the dispensing mechanism is released.

In the needle pre-use position the needle may be flush with the distal end of the body or the needle may be recessed within the body. In another embodiment the needle may be fixed in position relative to the body.

In another device, different features may be provided to prevent the actuation member from moving distally. For example, the stop may be provided on another component of the medicament delivery device. In another device a lock ring 216 is not present.

According to some embodiments of the present disclosure, an exemplary drug delivery device 10 is shown in FIGS. 1A & 1B. The device 10, as described above, is configured to inject a medicament into a patient's body. The device 10 includes a housing 11 which typically contains a reservoir containing the medicament to be injected (e.g., a syringe) and the components required to facilitate one or more steps of the delivery process. The device 10 can also include a cap assembly 12 that can be detachably mounted to the housing 11. A user typically removes the cap assembly 12 from the housing 11 before the device 10 can be operated. As shown, the housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

The device 10 can also include a needle sleeve 13 coupled to the housing 11 to permit movement of the sleeve 13 relative to housing 11. For example, sleeve 13 can move in a longitudinal direction parallel to longitudinal axis X. Specifically, movement of sleeve 13 in a proximal direction can permit a needle 17 to extend from the distal region 20 of the housing 11. Insertion of the needle 17 can occur via several mechanisms. For example, the needle 17 may be fixedly located relative to the housing 11 and initially be located within an extended needle sleeve 13. Proximal movement of the sleeve 13 by placing a distal end of the sleeve 13 against a patient's body and moving the housing 11 in a distal direction will uncover the distal end of the needle 17. Such relative movement allows the distal end of the needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to the housing 11. Such insertion can be triggered by movement of the sleeve 13 or by another form of activation, such as, for example, a button 22. As shown in FIGS. 1A & 1B, the button 22 is located at a proximal end of the housing 11. However, in other embodiments, the button 22 could be located on a side of the housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through the needle 17. In some embodiments, a drive spring (not shown) is under compression before the device 10 is activated. A proximal end of the drive spring can be fixed within the proximal region 21 of the housing 11, and a distal end of the drive spring can be configured to apply a compressive force to a proximal surface of the piston 23. Following activation, at least part of the energy stored in the drive spring can be applied to the proximal surface of the piston 23. This compressive force can act on the piston 23 to move it in a distal direction. Such distal movement acts to compress the liquid medicament within the syringe, forcing it out of the needle 17. Following injection, the needle 17 can be retracted within the sleeve 13 or the housing 11. Retraction can occur when the sleeve 13 moves distally as a user removes the device 10 from a patient's body. This can occur as the needle 17 remains fixedly located relative to the housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe to move it in a proximal direction. Following sufficient retraction, any relative movement between the needle 17 and the housing 11 can be locked with a locking mechanism. In addition, the button 22 or other components of the device 10 can be locked as required.

FIGS. 2A to 2G show the sequential steps of operating a medicament delivery device 200. The medicament delivery device 200 is an autoinjector.

The device 200 comprises a body 201, a syringe 250 having a needle 217 and an axially moveable plunger 223 for dispensing medicament from the syringe 250. The device comprises a cap 254 which is removably attached to the body 201 and covers a distal end 202 of the body 201 for preventing access to the needle 217. The device has a needle shield 266 that covers the needle 217 before use. The needle shield 266 is attached to the cap 254.

The medicament delivery device 200 has a dispensing mechanism 229. The medicament delivery device 200 has an actuation member 227 which is configured to release the dispensing mechanism 229. The actuation member 227 is configured to engage the dispensing mechanism 229 to release the dispensing mechanism 229.

The dispensing mechanism 229 is configured to cause the needle 217 to move distally from a needle pre-use position, in which the needle 217 is recessed within the body 201, to an injection position in which the needle 217 protrudes from the distal end 202 of the body 201 when the dispensing mechanism 229 is released.

The dispensing mechanism 229 is configured to dispense the medicament from the needle 217 when the needle 217 is in the injection position.

Figures 2A, 2B, 2C, 2D:
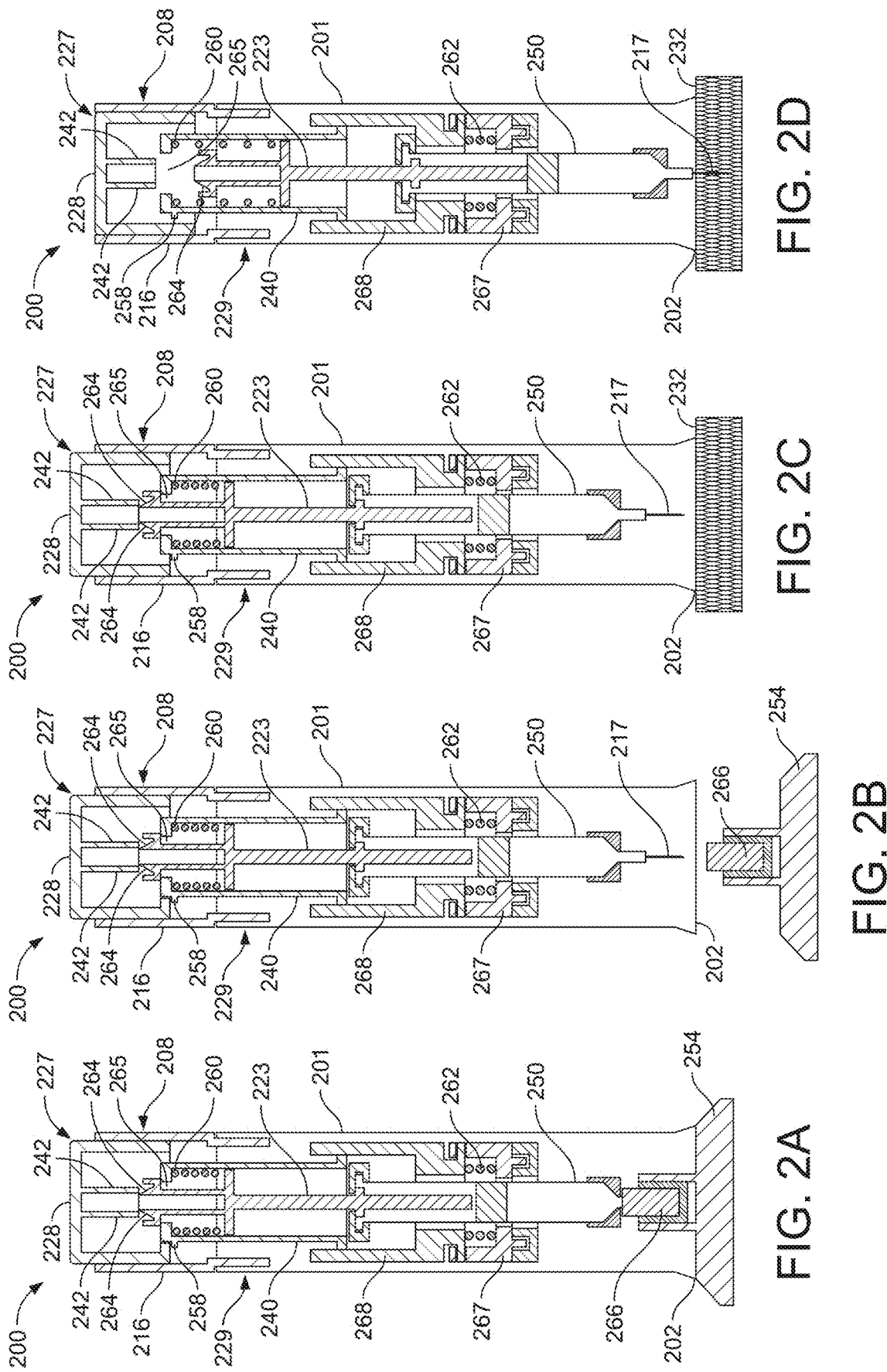
FIG. 2A is a schematic view of a medicament delivery device prior to use (i.e. in a pre-use configuration)
FIG. 2B is a schematic view of the device of FIG. 2A with the cap removed.
FIG. 2C is a schematic view of the device of FIG. 2A showing the device placed at an injection site.
FIG. 2D is a schematic view of the device of FIG. 2A with the button having been pressed to release the dispensing mechanism.

As shown in FIGS. 2B-2C, in order to deliver a dose of medicament to an injection site, the cap 254 is removed (FIG. 2B) and the device is placed at an injection site 232 (FIG. 2C).

The actuation member 227 comprises a button 228 and is prevented from being depressed by a stop 258. The stop is provided on the spring guide 240, for example.

The device has a locking member 208 in the form of a lock ring 216 which is rotatable by a user about a longitudinal axis of the device. The actuation member 227 is keyed to the lock ring 216 so that the actuation member 227 rotates with the lock ring 216. The lock ring 216 is rotatable from a pre-use position, in which distal movement of the button 228 is prevented, to a use position in which distal movement of the button 228 is permitted.

When the lock ring 216 is in the pre-use position then the stop 258 engages the button 228 to prevent the button 228 from being depressed.

In order to allow the button 228 to be depressed, the lock ring 216 is rotated about the longitudinal axis of the device from the pre-use position to the use position. The rotation of the lock ring 216 also rotates the actuation member 227 to a position in which the stop 258 no longer prevents the button 228 from being depressed as shown, for example, in FIG. 2C.

Turning now to FIG. 2D, the user then presses the button 228 to release the dispensing mechanism 229 for dispensing medicament from the device. The dispensing mechanism 229 has a plunger 223 and a bias in the form of a compression spring 260. The plunger 223 is biased distally by the spring 260.

The dispensing mechanism 229 is at least partially housed within the spring guide 240. The plunger 223 has a release member which has proximally-extending clips 264. The spring 260 is retained in the compressed position by virtue of the clips 264 which protrude through a proximal opening 265 in the spring guide 240. The clips 264 engage the spring guide 240 for maintaining the plunger 223 in a proximal position.

The actuation member 227 has a firing member comprising a pair of protrusions 242 which engage with the clips 264 when the button 228 is depressed to flex the clips 264 radially inwardly thereby allowing the clips 264 to move distally through the proximal opening 265 to release the spring 260.

When the dispensing mechanism 229 is released, then the syringe 250 is released for distal axial movement towards the injection site 232 such that the needle 217 moves from the needle pre-use retracted position to an exposed (or "uncovered" or "injection") position for delivering medicament to the injection site 232 under the biasing force of the compression spring 260.

Figure 2G:
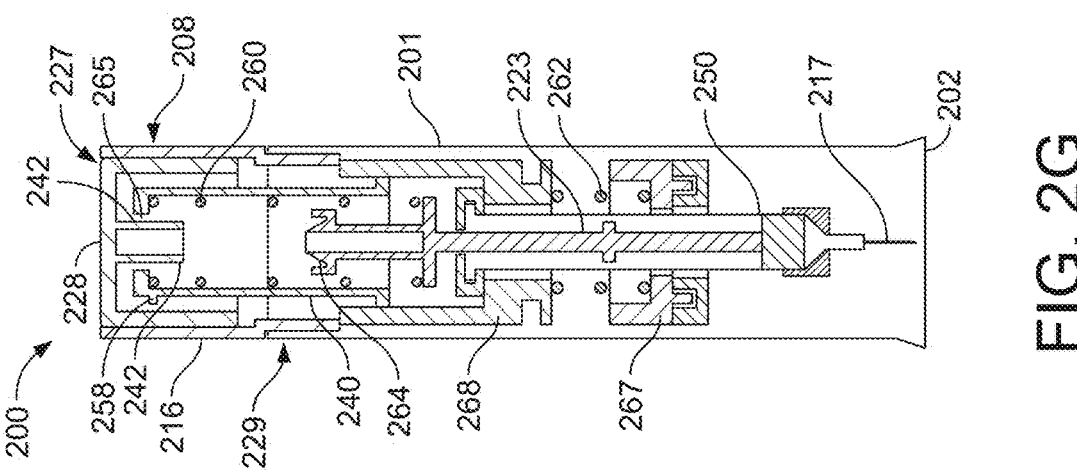
FIG. 2G is a schematic view of the device of FIG. 2A showing the device removed from the injection site after the needle has retracted within the device after delivery of the medicament.
Figure 2F:
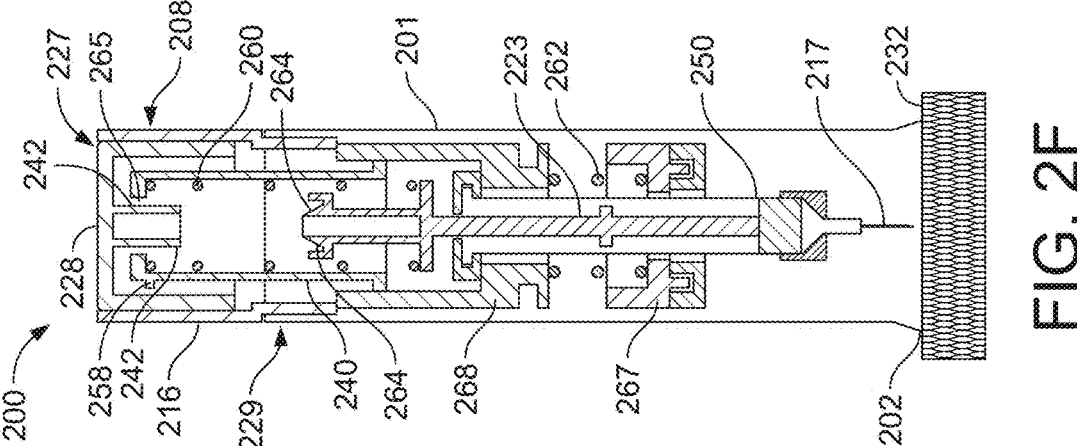
FIG. 2F is a schematic view of the device of FIG. 2A showing the needle having retracted within the device after a dose has been delivered.
Figure 2E:
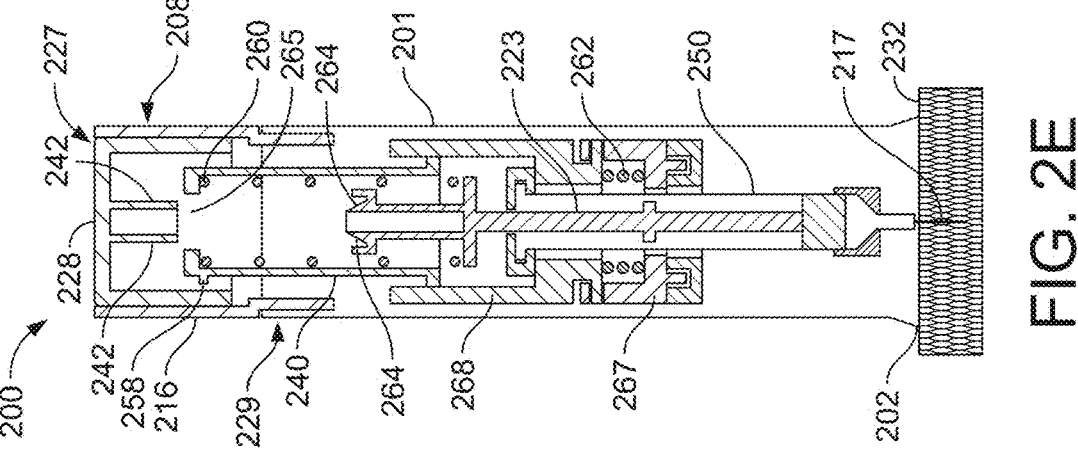
FIG. 2E is a schematic view of the device of FIG. 2A with the button having been pressed to release the dispensing mechanism.

Depressing the button 228 releases the plunger 223 which, biased by the bias 260, moves along the syringe 250 towards the distal end of the device 200 to force medicament within the syringe 250 through the needle 217, thereby delivering a dose of medicament as shown, for example in FIG. 2E.

As shown in FIG. 2F, once the dose of medicament has been delivered, a medicament container bias 262, embodied by a further spring 262, then causes the needle 217 to move axially back to the retracted position, away from the injection site 232 in a proximal direction. The plunger 223 flexes a clip (not shown) on a first collar 267 which allows the first collar 267 to rotate relative to the body 201 and relative to a second collar 268. The first collar 267 rotates from a first position in which the second collar 268 is axially coupled to the first collar 267, into a second position in which the second collar 268 is free to move axially relative to the first collar 267. For example, the second collar 268 may comprise a radially protruding coupling element configured to be received in or engage with a corresponding receiving portion of the first collar 267, such that rotating the first collar 267 from the first position into the second position causes the coupling element to be moved out from the receiving portion, to allow the second collar 268 to move axially relative to the first collar 267. Axial movement of the second collar 268 permits the needle 217 to be retracted.

As shown in FIG. 2G, the device 200 is then removed from the injection site 232, for disposal.

The medicament delivery devices described herein may have some or all of the features as described in relation to the medicament delivery device 200.

The dispensing mechanism 229 may have the some or all of the features as described and/or contemplated in relation to FIGS. 2A to 2G.

In another embodiment, the dispensing mechanism may have alternative or additional features to those described and/or contemplated in relation to FIGS. 2A to 2G. The dispensing mechanism may have features as described and/or contemplated herein, for example in relation to FIGS. 1A and 1B.

Figures 3A, 3B, 3C, 3D, 3E, 3F:
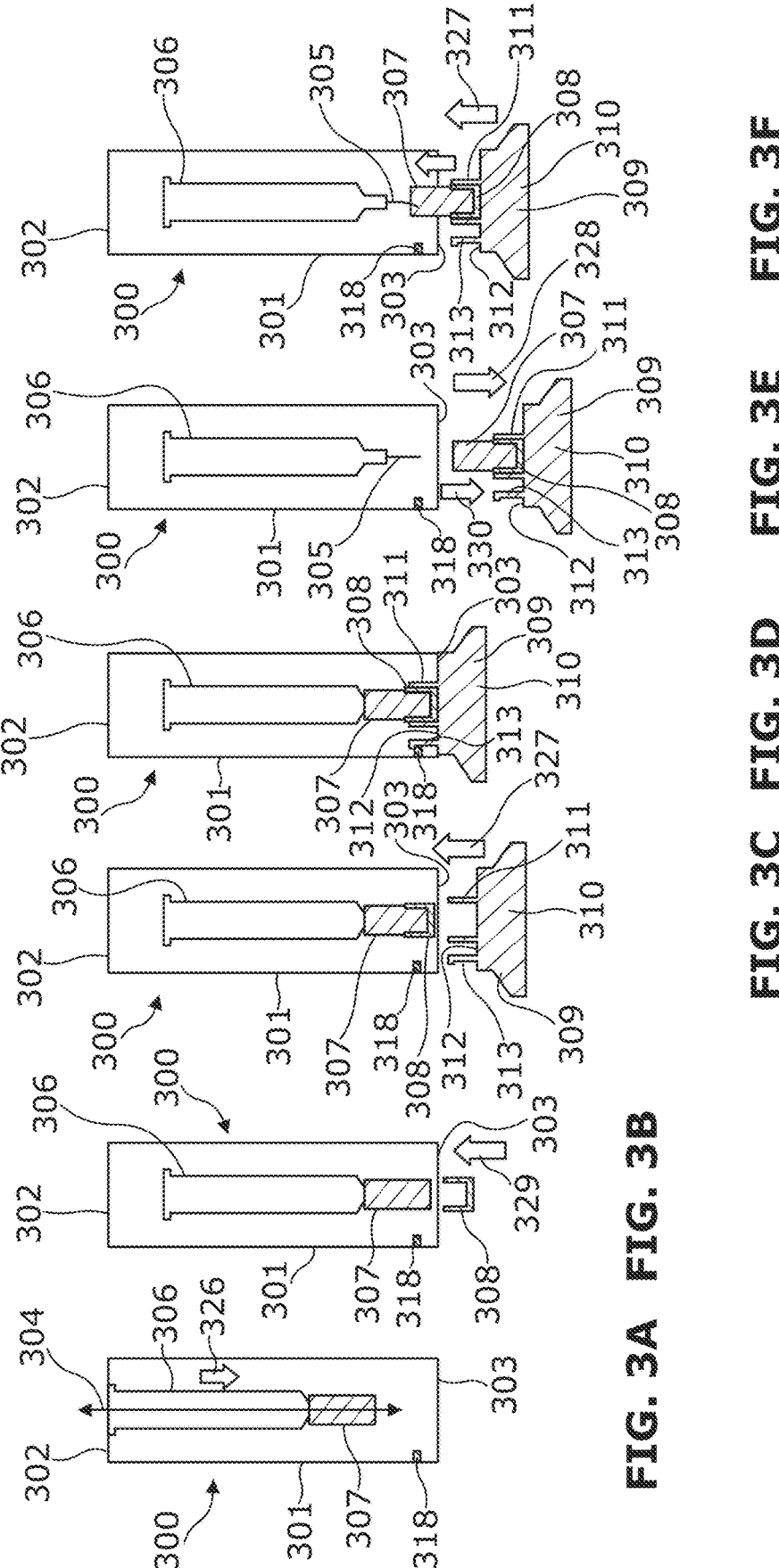
FIG. 3A shows a schematic cross-sectional view of a medicament delivery device in a pre-assembled state.
FIG. 3B shows a schematic cross-sectional view of a medicament delivery device in a pre-assembled state.
FIG. 3C shows a schematic cross-sectional view of a medicament delivery device with the cap uncapped.
FIG. 3D shows a schematic cross-sectional view of a medicament delivery device with the cap capped.
FIG. 3E shows a schematic cross-sectional view of a medicament delivery device with the cap removed.
FIG. 3F shows a schematic cross-sectional view of a medicament delivery device with the cap removed and the needle bent.

FIG. 3A shows a medicament delivery device 300 which may be generally similar to the medicament delivery device 200 described above, and which may operate in a similar manner. The medicament delivery device 300 comprises a body 301 having a proximal end 302 and a distal end 303 which define a longitudinal direction 304, and inside which is arranged a pre-filled syringe 306. The pre-filled syringe 306 comprises a needle 305 for injecting medicament into a user and configured to be arranged in an injecting position (which may also be referred to as an "exposed" or "uncovered" position) in which the needle protrudes from the distal end 303 of the body 301, for example as shown in FIG. 2E and described above. It is to be understood that the needle 305 and the pre-filled syringe 306 may be configured to function in substantially the same way as and be actuated in and operated in substantially the same way as the needle 305 and the pre-filled syringe 306 described above in relation to FIGS. 2A to 2G. It is also envisaged that the needle 305, the pre-filled syringe 306 and the body 301 may though be different from the needle 217, syringe 250 and body 201 described above. The pre-filled syringe 306 may be movable along the longitudinal direction 304 relative to and inside the body 301 along the direction 326 in order to prepare the medicament delivery device 300 for use.

Like the medicament delivery device 200 described above in relation to FIGS. 2A to 2G, the medicament delivery device 300 also comprises a cap 309, which may be fitted to the body 301 in a substantially similar way to the cap 254 described above and shown in FIG. 2A, to selectively cover the distal end 303 of the body 301 and conceal the needle 305. The cap 309 is moveable relative to the body 301 along the longitudinal direction 304 and is arrangeable in a capped position (see FIG. 3D for example) in which the cap 309 conceals the distal end 303 of the body 301, and an uncapped position (see FIGS. 3C, 3E and 3F) for example, in which at least a portion of the cap 309 is spaced apart from the distal end 303 of the body 301. It is to be understood that when the cap 309 is referred to as being in the "uncapped position", the cap 309 need not necessarily always be spaced apart from the distal end 303 of the body 301 by the same amount of spacing. That is, multiple positions of the cap 309 may be referred to as "an/the uncapped position", albeit in all such positions, a contact surface 312 of the cap 309 does not abut the distal end 303 of the body 301, such that the distal end 303 of the body 301 is not concealed by the cap 309. For example, FIG. 3C shows the cap 309 in an uncapped position in which the cap 309 is spaced apart from the distal end 303 by a smaller spacing than in the uncapped position shown in FIG. 3E.

Turning now to FIG. 3B, the medicament delivery device 300 further comprises a needle cover 307 and a cap insert 308. The needle cover 307 and the cap insert 308 may be collectively referred to as a "needle shield assembly". In the example shown, the needle cover 307 is generally cylindrical and hollow. Although it is envisaged that the needle cover 307 may have any other suitable shape or form. The needle cover 307 is slidably receivable inside the body 301 such that the needle cover 307 may be moved relative to the body 301 along the longitudinal direction 304. When the needle cover 307 is arranged inside the body 301, for example as shown in FIG. 3B, the needle cover 307 is arranged to circumscribe at least a portion of the needle 305. The cap insert 308 is also generally cylindrical in the example shown, although other shapes and forms are also possible. The cap insert 308 is configured to receive the needle cover 307, circumscribing a portion of the needle cover 307, and in turn, the cap insert 308 is configured to be received by the cap 309. In this manner, as shown sequentially in FIGS. 3B to 3D and as shall be described below in more detail, the cap insert 308 may be moved along the longitudinal direction 204 to fit it to the needle cover 307 such that the needle cover 307 is received inside the cap insert 308, and then the cap 309 may be moved along the longitudinal direction 304 towards the needle shield assembly (comprising the needle cover 307 and the cap insert 308) such that the cap insert 308 is received in the cap 309. In this manner, the needle cover 307 and the cap insert 308 are configured to be coupled to the cap 309. The needle cover 307, the cap insert 308 and the cap 309, are configured to be arranged concentrically relative to one another, relative to a central longitudinal axis of the body 301, such that the cap 309 is configured to concentrically receive the cap insert 308, and the cap insert 308 is configured to concentrically receive the needle cover 307. The cap insert 308 and the needle cover 307 may be received in the cap 309 via an interference fit when coupled thereto, such that once the cap insert 308 is received in and coupled to the cap 309, together with the needle cover 307, movement of the cap 309 along the longitudinal direction 304 will also cause the needle cover 307 and the cap insert 308 to move together with the cap 309.

Referring now to FIG. 3C, the body 301 is generally cylindrical in the example shown, although other shapes and forms may also be employed. A body clip interface 318 is arranged on an inner surface of the body 301 and protrudes radially inwards towards a central longitudinal axis of the body 301. In the example shown, the body 301 comprises a single discrete body clip interface 318, although it is also envisaged that the body 301 may comprise any number of one or more discrete body clip interfaces 318 angularly spaced around the circumference of the body 301, or a single generally annular body clip interface 318 arranged to circumscribe the entire circumference of the body 301. In any case, each of the one or more body clip interfaces 318 is configured to engage with an arm 313 of the cap 309 to selectively block movement of the cap 309 along the longitudinal direction, as shall be described below.

Turning back to FIG. 3A, the medicament delivery device 300 is shown in a pre-assembled state in which the pre-filled syringe 306, the needle 305 and the needle cover 307 are in a retracted position. At this stage, the cap insert 308 and the cap 309 are decoupled from the pre-filled syringe 306, hence the distal end 303 of the body 301 is exposed. The pre-filled syringe 306 may then be moved along the longitudinal direction 304 relative to the body 301 to place the pre-filled syringe 306 in a pre-use state, for example as shown in FIG. 2E and described above. By moving the cap insert 308 along the direction shown by the arrow 329 in FIG. 3B, the cap insert 308 may then be fitted to the needle cover 307 such that the cap insert 308 receives the needle cover 307 in an interference fit, as shown in FIG. 3C.

With further reference to FIG. 3C, the cap 309 may then be fitted into the capped position by moving the cap 309 in the direction of the arrow 327 towards the distal end 303 of the body 301, into the position shown in FIG. 3D. As the cap 309 is moved from the uncapped position shown in FIG. 3C into the capped position shown in FIG. 3D, the arm 313 of the cap 309 is configured to flex or otherwise deflect or deform relative to the body clip interface 318, such that when the cap 309 is in the position shown in FIG. 3D, the arm 313 is arranged to form a snap fit connection with the body clip interface 318. This may be achieved, for example, by a free end of the arm 313 comprising a widened or thickened portion which is configured to be blocked or impeded by the body clip interface 318, thus necessitating said flexing, deflecting or deformation. The widened or thickened portion may be relatively short compared with the entire length of the arm 313, for example the widened or thickened portion may comprise up to about a quarter of the length of the arm 313, for example about a fifth or a sixth of said length, such that the arm 313 may be deflected relatively easily around the body clip interface 318 to form a two-way snap-fit connection therewith. In the position shown in FIG. 3D, the cap 309 is in the capped position and receives the cap insert 308 in an interference fit, hence the cap 309 is coupled to the cap insert 308 and the needle cover 307. The cap 309 is also coupled to the body 301, via the body clip interface 318, by means of said snap fit connection. Though, it is envisaged that the cap 309, for example the arm 313 thereof, may also be coupled to the body 301 in any other suitable way. In the position shown in FIG. 3D, the medicament delivery device 300 is in an assembled state, pre-use, i.e. pre-injection, before any medicament has been injected by the needle 305.

Next, as shown in FIG. 3E, in order to prepare the medicament delivery device 300 for use, the cap 309 must be removed, so that the distal end 303 of the body 301 and the needle 305 may be exposed, for example as described above in relation to FIGS. 2A and 2B. The cap 309 may be removed and placed into the uncapped position by moving the cap 309 along the longitudinal direction 304 along the direction shown by the arrow 328. At this time, because the cap 309 is coupled to the cap insert 308 and the needle cover 307, which are received by the cap 309, for example in a concentric interference fit, this means that longitudinal movement of the cap 309 relative to the body 301 causes corresponding movement of the cap insert 308 and the cap 309. Thus, the needle cover 307 and the cap insert 308 also move along the longitudinal direction 304, in the direction shown by the arrow 330. To move the arm 313 of the cap 309 between the positions shown in FIGS. 3D and 3E, the arm 313 may similarly flex, deflect or otherwise deform relative to the body clip interface 318, in a reverse motion as would occur sequentially between the positions shown in FIGS. 3C and 3D, in order to decouple the aforementioned snap fit connection. At the stage shown in FIG. 3E, the cap 309 is no longer in the capped position, and the needle cover 307 has been removed from the needle 305, thus the needle 305 is uncovered and the medicament delivery device 300 is ready for injection to commence.

Turning now to FIG. 3F, the user of the medicament delivery device 300 may then subsequently attempt to re-fit the cap 309 to the body 301, thus moving the cap 309 back into the capped position. The user may attempt this, for example, after the medicament delivery device 300 has already been used to deliver medicament from the needle 305, or before medicament has been dispensed from the needle 305. For example, in the case of the latter, the user might remove the cap 309 from the body 301, into the uncapped position, but they may not be ready for the medicament to be administered and may wish to actually dispense the medicament via the needle 305 at a later time, in which case they may then decide to recap the cap 309 onto the body 301. In the medicament delivery device 300 shown in FIGS. 3A to 3F, it is possible to re-cap the cap 309 pre or post use of the medicament delivery device 300 (i.e. pre or post medicament delivery). However, as shown in FIG. 3F, this risks bending or otherwise damaging the needle 305. FIG. 3F illustrates the needle 305 in a bent, damaged position. Re-capping pre-use may lead to a bent needle 305, which may result in injection pain and/or wet injection if the needle 305 is then used to deliver medicament. A bent needle may also result in wasted medicament. Ways in which the risk of bending the needle 305, by preventing re-capping, i.e. by preventing the cap 309 from being re-fitted into the capped position once it has already been removed from the body 301 into the uncapped position, shall now be described, with reference to the subsequent figures.

Figures 4, 5A, 5B, 5C, 5D, 5E:
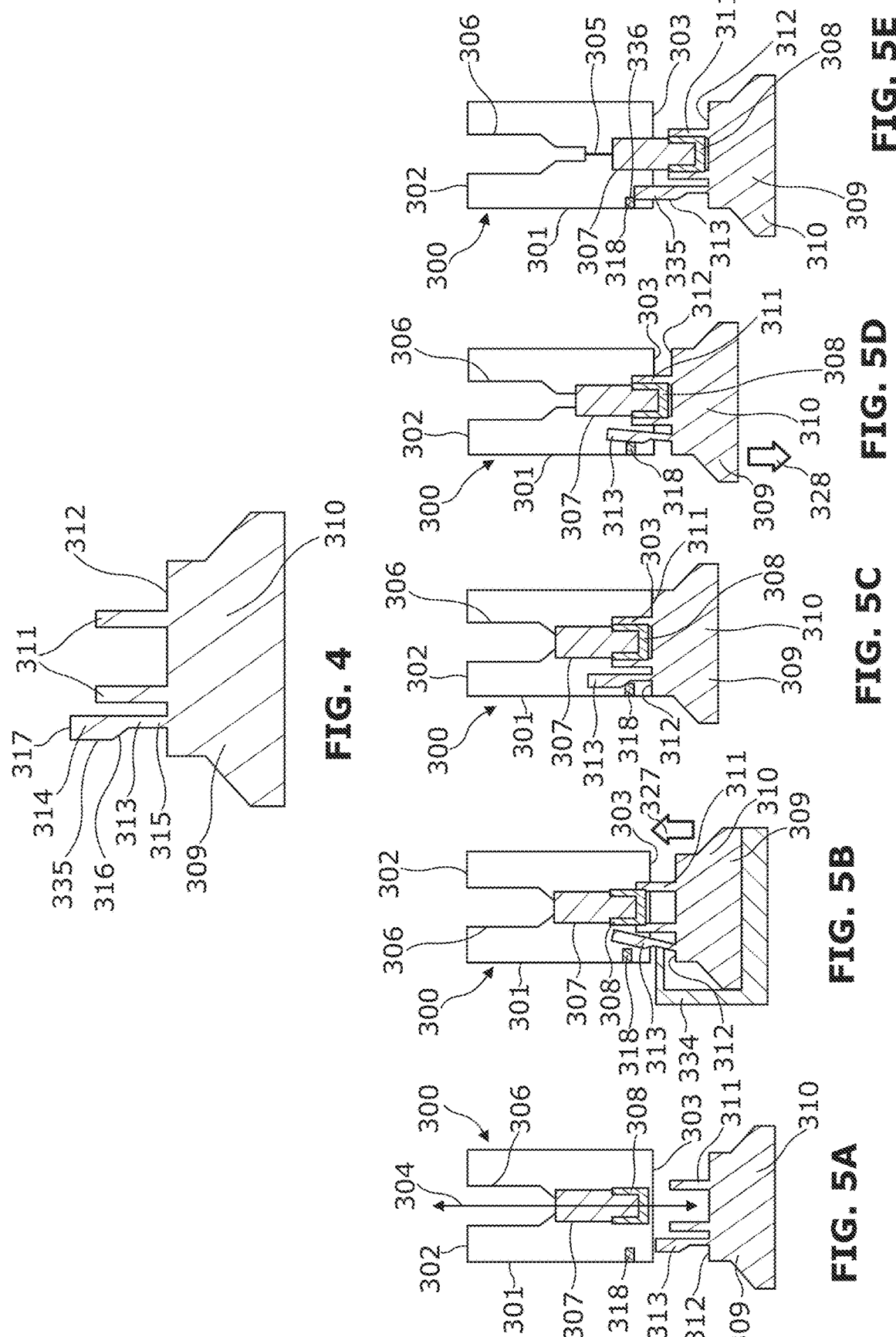
FIG. 4 shows a schematic cross-sectional view of a cap.
FIG. 5A shows a schematic cross-sectional view of a medicament delivery device in a pre-assembled state.
FIG. 5B shows a schematic cross-sectional view of a medicament delivery device during assembly of the cap.
FIG. 5C shows a schematic cross-sectional view of a medicament delivery device with the cap capped.
FIG. 5D shows a schematic cross-sectional view of a medicament delivery device during removal of the cap.
FIG. 5E shows a schematic cross-sectional view of a medicament delivery device with the cap uncapped.

FIG. 4 shows a cross-sectional view of a cap 309 which comprises a body portion 310 configured to be held by a user, and a receiving portion 311 configured to circumscribe and circumferentially receive the cap insert 308, as with the cap 309 and cap insert 308 described above in relation to FIGS. 3A to 3F for example. In the example shown, the cap 309 has a generally circular cross-sectional profile in a plane that is normal to the longitudinal direction 304, although it is envisaged that the cap 309 may have any other suitable shape or form. The receiving portion 311 is arranged to protrude from the body portion 310, and in the example shown, is generally hollow and cylindrical. The cap 309 further comprises a generally flat contact surface 312, which is oriented to be generally flat in a plane that is normal to the longitudinal direction 304. The contact surface 312 is configured to contact and abut the distal end 303 of the body 301, for example as shown in FIG. 3D, when the cap 309 is in the capped position. When the cap 309 is in an uncapped position, the contact surface 312 is configured to be spaced apart from the distal end 303 of the body 301, and may be generally parallel relative thereto.

The cap 309 further comprises an arm 313 comprising a fixed end 315 that is fixed to or integrally formed with the body portion 310, and a free end 314 opposite to the fixed end 315. In the example shown, the cap 309 comprises a single arm 313, however it is also envisaged that the cap 309 may comprise any number of one or more arms 313, which may be angularly spaced apart from one another relative to the circumference of the cap 309. For example, the cap 309 may comprise two arms 313 which are equally spaced apart from one another to be arranged on opposite sides of the cap 309. The arm 313 differs from the arm 313 shown in FIGS. 2A to 2F in that the free end 314 of the arm is sized and shaped to act as a blocking element, to selectively impede movement of the cap 309 along the longitudinal direction 304 into the capped position, by being configured to form a one-way snap fit connection, rather than a two-way snap fit connection, with the body clip interface 318. For example, the widened or thickened portion of the arm 313, which comprises the free end 314, may extend over a larger proportion of the entire length of the arm 313 than in the example of FIGS. 3A to 3F. For example, the widened or thickened portion of the arm 313 may extend over about at least a third of the proportion of the entire length of the arm 313, for example about at least a half thereof. The width/thickness of the widened or thickened portion of the arm 313 may be configured to be greater than the relatively narrower/thinner portion of the arm 313 at the fixed end 315, and may for example be approximately twice the thickness/width of said portion, as shown in the example of FIG. 4. The free end 314 may thus be configured to be more rigid than in the example of FIGS. 3A to 3F, and the geometry of the free end 314 may be sized and shaped relative to the body clip interface 318 such that an additional action or force is required to flex, deflect or deform the free end 314 relative to the body clip interface 318 to fit the arm 313 into the one-way snap-fit connection.

In order to configure the arm 313 such that its size and shape relative to the body clip interface 318 provides for such a one-way snap-fit connection, the arm 313 may be designed such that angular deflection, pivoting, or angular flexing, or other movement or displacement of the free end 314 relative to the fixed end 315 is required in order to fit the arm 313 around the body clip interface 318. For example, with reference to FIG. 5E, this may be achieved by an outermost surface 335 of the arm 313 being arranged to radially overlap with the body clip interface 318, such that an innermost surface 336 of the body clip interface 318 is arranged to be radially closer to a central longitudinal axis of the body 301 than the outermost surface 335 of the arm 313, such that the only way to move the arm 313 past the body clip interface 318 towards the proximal end 302 to place the cap 309 into the capped position, is to deflect or displace the arm 313 relative to the body clip interface 318 to cause the outermost surface 335 of the arm 313 to be arranged radially inwards relative to the innermost surface of the body clip interface 318, for example as shown in FIG. 5B.

With further reference to FIG. 4, the arm 313 also comprises a chamfered surface 316 which is angled relative to the longitudinal direction 304 and which is configured to facilitate movement of the arm 313 relative to the body clip interface 318, to facilitate deflection of the arm 313 relative thereto. That is, the chamfered surface 316 is configured to facilitate movement, such as sliding or translation, between the arm 313 and the body clip interface 318. In the example shown, the chamfered surface 316 is generally linear and straight, although it is also envisaged that the chamfered surface 316 may comprise a curved surface. The arm 313 also comprises a blocking surface 317, arranged at the free end 314, which in the example shown is generally flat in a plane generally normal to the longitudinal direction 304, and which is configured to abut the body clip interface 318 and engage therewith, to block movement of the cap 309 in the longitudinal direction 304 into the capped position, as described below.

FIG. 5A shows a medicament delivery device 300 which is substantially similar to that shown in FIGS. 3A to 3F and described above, although the cap 309 differs, because the cap 309 in the medicament delivery device 300 of FIGS. 5A to 5E is the cap 309 shown in FIG. 4 and described above. FIG. 5A shows the medicament delivery device 300 in a pre-assembled state in which the needle cover 307 is retracted inside the body 301 and the cap insert 308 is coupled to the needle cover 307, but the cap 309 is decoupled from the cap insert 308 and the body 301 and is in an uncapped position. In this initial position, the cap 309 is prevented from being able to move along the longitudinal direction 304 far enough for the contact surface 312 to contact and abut the distal end 303, because the free end 314 of the arm 313, which acts as a blocking element as described above, is sized and shaped relative to the body clip interface 318 such that the free end 314 blocks movement of the cap 309 into the capped position, because the blocking surface 317 will be obstructed from moving further along the longitudinal direction 304 by the body clip interface 318. Thus, in the example shown, in order to assemble the cap 309 into the capped position shown in FIG. 5C, a force can be applied to the arm 313, for example a generally radially inwards force that is generally normal to the longitudinal direction 304, in order to deflect the free end 314 of the arm 313 radially inwards, such that the arm 313 may be flexed, deflected or otherwise deformed around the body clip interface 318 in order to permit the cap 309 to be placed into the capped position. Said force may be applied, for example, by an additional external part such as an assembly fixture 334, jig or tool, as shown in FIG. 5B, to push the arm 313 inwards to flex it around the body clip interface 318. The assembly fixture 334, jig or tool may then subsequently be removed.

Thus, by application of said force, and movement of the cap 309 along the longitudinal direction 304 towards the distal end 303, the cap 309 can be arranged into the capped position as shown in FIG. 5C, in which the cap 309 receives the cap insert 308 and is coupled thereto and to the body 301, via the arm 313 and the body clip interface 318 forming a one-way snap-fit connection. FIG. 5C shows the medicament delivery device 300 in a pre-use state. Next, once the user is ready to use the medicament delivery device 300 to inject medicament via the needle 305, the cap 309 must be removed. FIGS. 5C to 5D sequentially show the removal of the cap 309 to move the cap 309 from the capped position into an uncapped position. The chamfered surface 316 on the arm 313 of the cap 209 permits the arm 313 to flex relative to the body clip interface 318 and disengage therewith such that the cap 309 may be moved away from the distal end 303 along the longitudinal direction 304, thus simultaneously pulling the cap insert 308 and the needle cover 307 out from the body 301 therewith. The chamfered surface 316 thus converts the axial movement of the cap 309 along the longitudinal direction 304 into a radial flex of the arm 313.

Finally, comparing FIG. 5E with FIG. 3F and the above description thereof, at this stage, whether the user has or has not actually delivered any medicament via the needle 305, at this stage the user is blocked from being able to re-cap the device. That is, they are blocked from moving the cap 309 back into the capped position, thus avoiding the risk of bending the needle 305. The cap 309 is prevented from being placed back into the capped position because the blocking surface 317 of the arm 313 abuts against the body clip interface 318, thus impeding further longitudinal movement of the cap 309 towards the distal end 303 of the body 301.

In this manner, the free end 314 of the arm 313 of the cap 309 functions as a blocking element, wherein when the cap 309 is in an uncapped position, the blocking element, i.e. the free end 314 of the arm 313, is arrangeable in: a first state (see FIG. 5B) in which movement of the cap from the uncapped position into the capped position is permitted, and a second state (see FIG. 5E) in which movement of the cap 309 from the uncapped position into the capped position is prevented. Moving the cap 309 from the capped position (see FIG. 5C) into the uncapped position (see FIG. 5E) causes the blocking element, i.e. the free end 314 of the arm 313, to be arranged in the second state. That is, uncapping the cap 309, by moving it away from the distal end 303 along the longitudinal direction 304, as shown sequentially in FIGS. 5C to 5E, causes the arm 313 to flex around the body clip interface 318 back into its unflexed position, so that it is unable to move longitudinally past the body clip interface 318. In this manner, the arm 313, which may also be referred to as a clip, blocks re-capping of the cap 309. Whilst in the example shown, there is one arm 313 and one body clip interface 318, it is envisaged that the medicament delivery device 300 may comprise a plurality of arms 313 and corresponding respective body clip interfaces 318, for example any number of one, two, three, four, fix, sive, seven, eight or more such arms 313 and corresponding respective body clip interfaces 318. The arms 313 and body clip interfaces 318 may be angularly spaced apart from one another either regularly or irregularly such that they are rotationally patterned around a central longitudinal axis of the body 301. Advantageously, this may reduce off-centre bending forces.

FIGS. 6A to 6E show another example of a medicament delivery device 300 comprising a cap 309 according to the example of FIG. 4 described above. The medicament delivery device 300 of FIGS. 6A to 6E differs from that of FIGS. 5A to 5E in that instead of an assembly fixture 334 or other means being used to apply a radially inwards force to the arm 313 in order to push it inwards to flex it relative to the body clip interface 318 to fit the cap 309 into the capped position, the cap 309 is rotated to bring the arm 313 into alignment and engagement with the body clip interface 318. The cap 309 is configured to be initially moved along the direction shown by the arrow 327 to place it into an interference fit with the cap insert 308 and such that the contact surface 312 is in contact with the distal end 303 of the body 301, but at this stage (see FIG. 6B) the cap 309 is not yet coupled to the body 301 because the arm 313 has not yet been placed into a snap fit with the body clip interface

318. This is because in the position shown in FIG. 6B, the arm 313 is oriented to be angularly spaced apart from the body clip interface 318. The arm 313 and the body clip interface 318 need to be angularly aligned with one another in order to arrange them in the snap-fit connection.

Figures 6A, 6B, 6C, 6D, 6E:
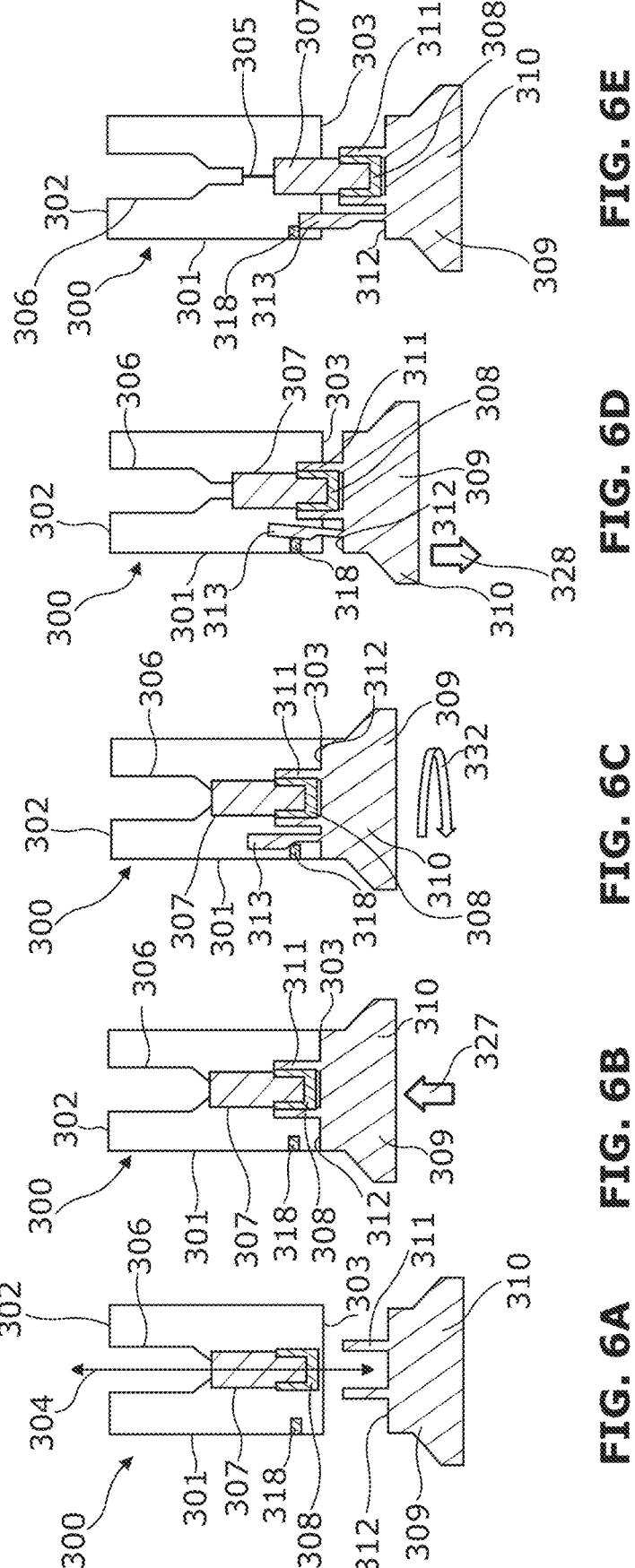
FIG. 6A shows a schematic cross-sectional view of a medicament delivery device in a pre-assembled state.
FIG. 6B shows a schematic cross-sectional view of a medicament delivery device with the cap capped.
FIG. 6C shows a schematic cross-sectional view of a medicament delivery device with the cap capped.
FIG. 6D shows a schematic cross-sectional view of a medicament delivery device during removal of the cap.
FIG. 6E shows a schematic cross-sectional view of a medicament delivery device with the cap uncapped.

Thus, the example of FIGS. 6A to 6E requires an additional assembly step to couple the cap 309 to the body 301 and properly place the cap 309 in a capped state. Referring now to FIGS. 6B to 6C, the cap 309 is then rotated relative to the body 301 along the direction shown by the arrow 332 to cause the arm 313 to rotate relative to the body clip interface 318. At the correct amount of rotational displacement, the arm 313 is caused to be aligned with the body clip interface 318, and since the cap 309 has already been moved along the longitudinal direction 304 such that the contact surface 312 is already in contact with and abutting the distal end 303 as shown in FIG. 6B, the arm 313, and in particular the free end 314 thereof, have already been displaced along the longitudinal direction 304 to the extent that the chamfered surface 316 is aligned with a proximal end of the body clip interface 318. That is, the step shown in FIG. 6B axially moves the cap 309 into contact with the distal end 303 such that the arm 313 and the chamfered surface 316 thereof are already at the correct longitudinal displacement to be aligned with the body clip interface 318. Thus, no bending, flexing, deflection or deformation of the arm 313 is needed in order to place it in a one-way snap-fit connection with the body clip interface 318. Instead, the arm 313 merely needs to be angularly displaced by rotating the cap 309 to bring the chamfered surface 316 into contact with the body clip interface 318, into the position shown in FIG. 6C, in which the cap 309 is in the capped position. Next, as shown in FIGS. 6D and 6E, the cap 309 may be removed by moving it away from the distal end 303 along the longitudinal direction 304, which causes the arm 313 to deflect around the body clip interface 318; such that once the cap 309 has been removed, the arm 313 is undeflected and the blocking surface 317 and the body clip interface 318 are configured to abut one another to prevent the user from placing the cap 309 back into the capped position, as also shown in FIGS. 5D and 5E and described above in relation thereto.

In the example shown in FIG. 6C and described herein, in order to bring the arm 313 into angular alignment with the body clip interface 318 after the cap 309 has already been moved along the longitudinal direction 304 to bring the contact surface 312 into contact with the distal end 303, the cap 309 is rotated relative to the body 301. However, it is also envisaged that the body 301 and/or the body clip interface 318 may instead be rotated relative to the cap 309 in order to place the arm 313 of the cap 309 and the body clip interface 318 into this alignment. It is also envisaged that both the cap 309 and the body 301 or the body clip interface 318 may be rotated relative to one another. For example, the body clip interface 318 may be coupled to or integrally formed with a collar which may be rotatable relative to the cap 309 and to the body 301. It is to be understood that what is required is some kind of relative motion between the arm 313 and the body clip interface 318, and that this motion may be rotational motion, and may be motion of the arm 313, the body clip interface 318, and/or the body 301.

Furthermore, whilst in the example shown in FIGS. 6A to 6E, there is one arm 313 and one body clip interface 318, it is envisaged that the medicament delivery device 300 may comprise a plurality of arms 313 and a plurality of corresponding respective body clip interfaces 318, for example any number of one, two, three, four, five, six, seven, eight or more such arms 313 and corresponding respective body clip interfaces 318. The arms 313 and body clip interfaces 318 may be angularly spaced apart from one another either regularly or irregularly such that they are rotationally patterned around a central longitudinal axis of the body 301. Advantageously, this may reduce off-centre bending forces.

FIGS. 7A to 7F show another exemplary medicament delivery device 300 which is substantially similar to that shown in FIGS. 6A to 6E and described above in relation thereto. In the example of FIGS. 7A to 7F, the cap 309 may be assembled onto the body 301 using a slightly different sequence of assembly steps. That is, in the example of FIGS. 6A to 6E, the cap 309 is moved towards the distal end 303 along the longitudinal direction 304 by the maximum possible displacement, such that the contact surface 312 is in contact with and abuts the distal end 303 (see FIGS. 6B), before any rotation of the cap 309 relative to the body clip interface 318 takes place (see FIG. 6C) to then place the arm 313 into rotational alignment with the body clip interface 318. Hence, no flexing or deflecting of the arm 313 is required relative to the body clip interface 318 in order to place the arm 313 and the body clip interface 318 into the one-way snap fit connection to fit the cap 309 into the capped position, because the arm 313 has previously already been brought into the correct longitudinal position relative thereto. However, in the example of FIGS. 7A to 7F, flexing or deflection of the arm 313 is required to fit the cap 309 into the capped position, because the cap 309 may be rotated relative to the body clip interface 318 before the contact surface 312 is brought into contact with the distal end 303.

Figures 7A, 7B, 7C, 7D, 7E, 7F:
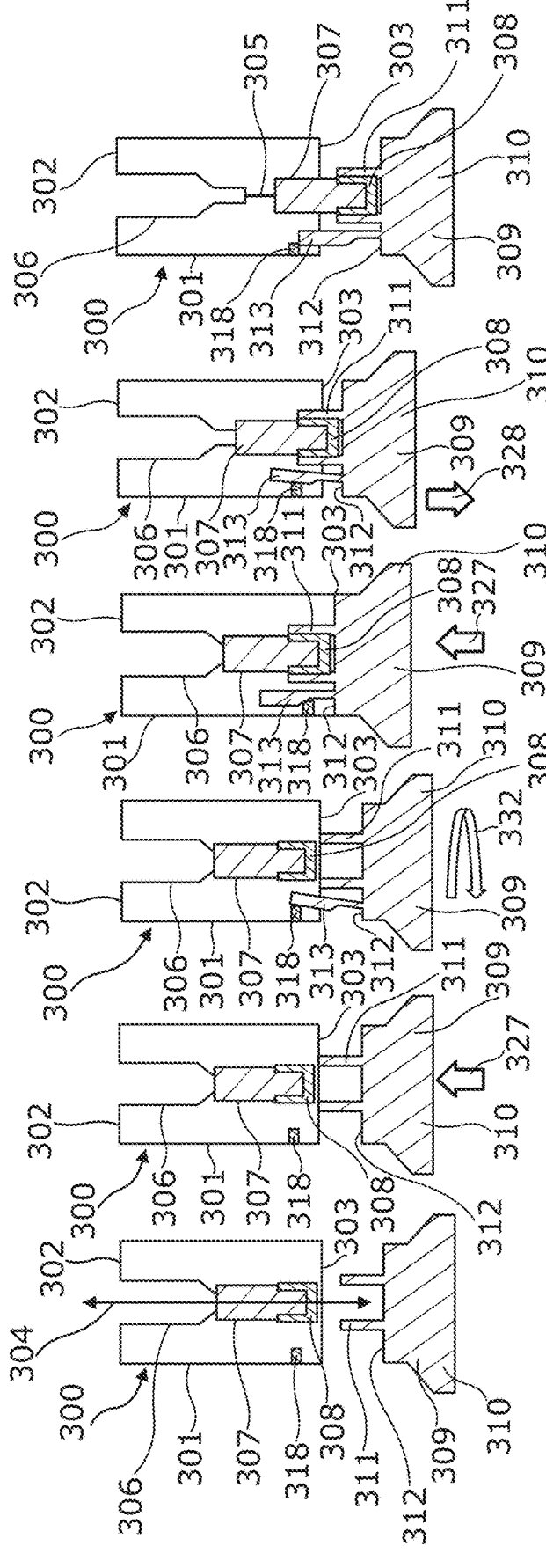
FIG. 7A shows a schematic cross-sectional view of a medicament delivery device in a pre-assembled state.
FIG. 7B shows a schematic cross-sectional view of a medicament delivery device during assembly.
FIG. 7C shows a schematic cross-sectional view of a medicament delivery device during assembly of the cap.
FIG. 7D shows a schematic cross-sectional view of a medicament delivery device with the cap capped.
FIG. 7E shows a schematic cross-sectional view of a medicament delivery device during removal of the cap.
FIG. 7F shows a schematic cross-sectional view of a medicament delivery device with the cap uncapped.

That is, FIG. 7A generally corresponds with FIG. 6A, then at the step shown in FIG. 7B, the cap 309 may be brought closer to the distal end 303 along the longitudinal direction 304 by moving the cap 309 in the direction shown by the arrow 327, but such that the contact surface 312 is still spaced apart from the distal end 303. For example, as shown in FIG. 7B, the cap 309 may be longitudinally displaced relative to the body 301 to such an extent that the receiving portion 311 contacts and abuts the distal end 303. Next, as shown in FIG. 7C, the cap 309 may be rotated relative to the body 301 (or alternatively, the body 301 and/or the body clip interface 318 may be rotated relative to the cap 309 as described above) in order to bring the arm 313 into angular alignment with the body clip interface 318. Because at this stage the chamfered surface 316 is not yet longitudinally aligned with the body clip interface 318, the arm 313 has to be flexed or deflected to fit it around the body clip interface 318, as shown in FIG. 7C, as the cap 309 is then also moved further towards the distal end 303 along the longitudinal direction 304 along the direction shown by the arrow 327 into the position shown in FIG. 7D. The cap 309 may then subsequently be removed, and prevented from being placed back into the capped position, as shown in FIGS. 7E and 7F, in the same manner as shown in FIGS. 5D and 5E and 6D and 6E and described above in relation thereto.

Furthermore, whilst in the example shown in FIGS. 7A to 7F, there is one arm 313 and one body clip interface 318, it is envisaged that the medicament delivery device 300 may comprise a plurality of arms 313 and a plurality of corresponding respective body clip interfaces 318, for example any number of one, two, three, four, five, six, seven, eight or more such arms 313 and corresponding respective body clip interfaces 318. The arms 313 and body clip interfaces 318 may be angularly spaced apart from one another either regularly or irregularly such that they are rotationally patterned around a central longitudinal axis of the body 301. Advantageously, this may reduce off-centre bending forces.

FIGS. 8A to 8D show another example of a medicament delivery device 300. The cap 309 of the medicament delivery device 300 of FIGS. 8A to 8D is substantially similar to that shown in FIGS. 4 to 7F and described above. However, the cap 309 differs in that the arm 313 need not necessarily include a chamfered surface 316. The arm 313 may include a chamfered surface 316, however in the example illustrated, no chamfered surface is present. This is because in the example shown in FIGS. 8A to 8D, the chamfered surface is instead provided on the body clip interface 318, in the form of a chamfered surface 319, which is angled relative to the longitudinal direction 304. Similarly to the chamfered surface 316 in the aforementioned examples, the chamfered surface 319 is configured to facilitate movement between the arm 313 and the body clip interface 318. In the example shown, the chamfered surface 319 is generally linear and straight, although it is also envisaged that the chamfered surface 319 may comprise a curved surface. The example of FIGS. 8A to 8D is similar to the example of FIGS. 6A to 6E in that in order to fit the cap 309 into the capped position and couple the cap 309 to the body 301, the cap 309 is first moved along the longitudinal direction 304 to bring the contact surface 312 into contact with the distal end 303, and the cap 309 and the body clip interface 318 are subsequently rotationally moved/angularly displaced relative to one another.

The example of FIGS. 8A to 8D differs from the previous examples in that the body clip interface 318 is in the form of a generally annular collar arranged to extend around the circumference of an inner surface of the body 301. The collar/body clip interface 318 is coupled to the body 301 but is rotationally movable relative thereto. The collar/body clip interface 318 is configured to be axially fixed relative to the body 301, such that it cannot move axially relative to the body 301. The collar/body clip interface 318 and the body 301 may be configured such that the range of motion of the collar/body clip interface 318 relative to the body 301 is limited. The collar/body clip interface 318 may be configured to be in an interference fit with the body 301, which can help prevent the collar/body clip interface 318 from unintentionally moving during use. In the example shown, the collar is generally annular and extends around the entire circumference of the body 301, however it is envisaged that the body clip interface 318 need not necessarily be a full annulus and may for example extend over a segment, i.e. a portion of, the circumference of the inner surface of the body 301. For example, the collar may be arranged to extend over at least 90° of said circumference, for example at least 180° thereof. In any case, it is to be understood that the collar has a first portion which does not comprise the chamfered surface 319, and a second portion which does comprise the chamfered surface 319. It is also envisaged that the collar may comprise a plurality of chamfered surfaces 318 spaced apart from one another. The chamfered surface 319 (or plurality thereof) functions to facilitate flexing, deflection or other deformation of the arm 313 relative to the body clip interface 318, in order to allow the cap 309 to be fitted into the capped position, as described below.

Figures 8A, 8B, 8C, 8D:
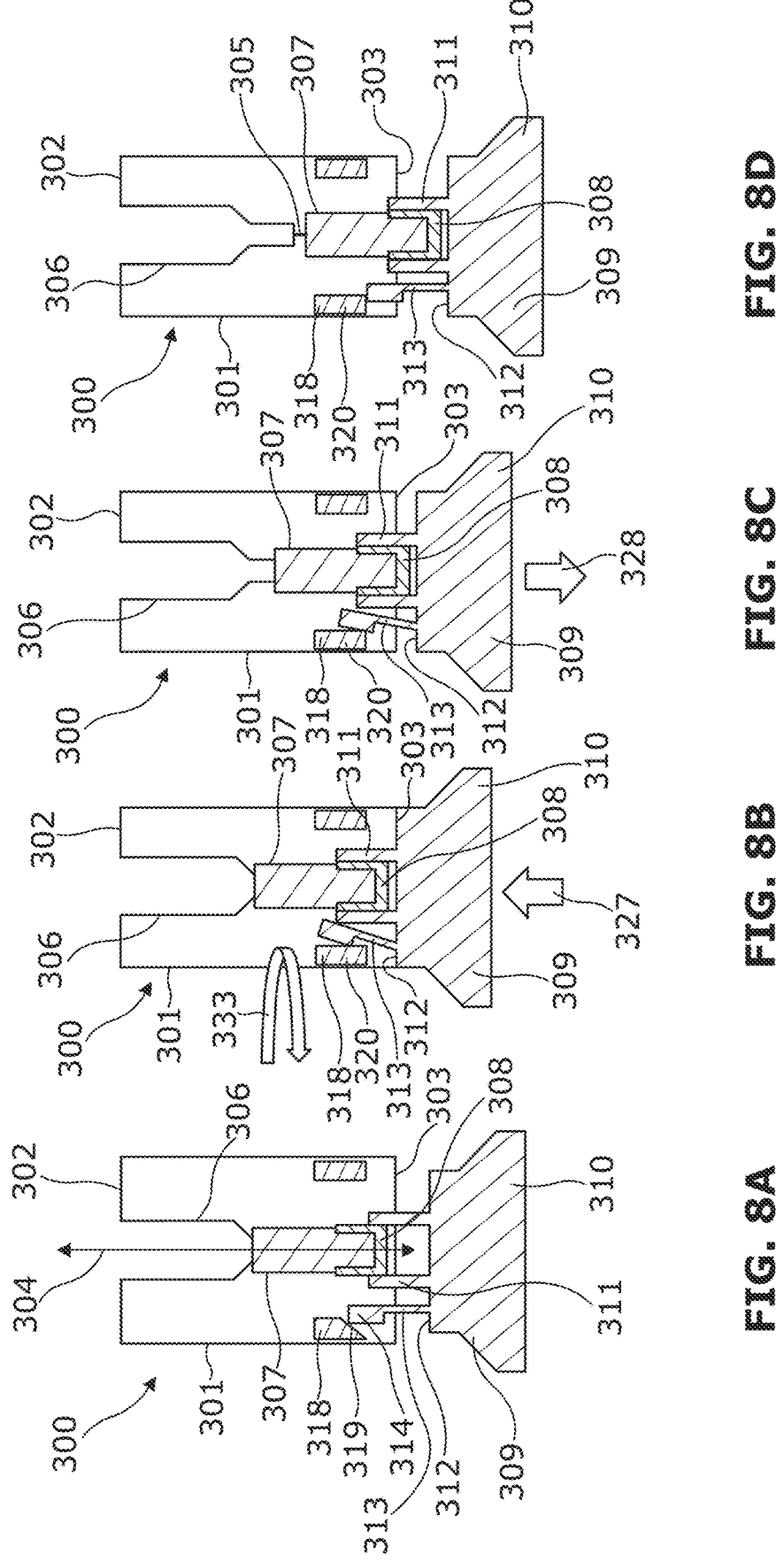
FIG. 8A shows a schematic cross-sectional view of a medicament delivery device in a pre-assembled state.
FIG. 8B shows a schematic cross-sectional view of a medicament delivery device with the cap capped.
FIG. 8C shows a schematic cross-sectional view of a medicament delivery device during removal of the cap.
FIG. 8D shows a schematic cross-sectional view of a medicament delivery device with the cap uncapped.

FIG. 8A shows the medicament delivery device 300 in an uncapped state in which the cap 309 is in an uncapped position and the contact surface 312 is spaced apart from the distal end 303 along the longitudinal direction 304. In the position shown, the arm 313 is angularly aligned with the portion of the collar/body clip interface 318, which comprises the chamfered surface 316. Thus, in this position, the body clip interface 318 and the arm 313 are aligned such that the free end 314 of the arm 313 and the chamfered surface

316 may move relative to one another. Next, as shown in FIG. 3B, the user may apply a force to the cap 309 to move the cap 309 along the longitudinal direction 304 further towards the distal end 303 along the direction shown by the arrow 327. As the cap 309 is moved closer towards the body 301, an upper outer vertice or edge of the free end 314 of the arm 313 will be caused to translate diagonally along the chamfered surface 319. This will cause the arm 313 to flex/deflect relative to the collar/body clip interface 318, which will simultaneously cause the collar/body clip interface 318 to rotate relative to the body 201, in the direction of the arrow 333 shown in FIG. 8B. This causes the chamfered surface 319 to be rotated away from the arm 313 such that the chamfered surface 319 and the arm 313 are no longer angularly aligned.

Thus, in the position shown in FIG. 8B, the arm 313 is instead aligned with another portion of the collar/body clip interface 318 which does not comprise the chamfered surface 319. In this position, the contact surface 312 is in contact with and abuts the distal end 303 of the body 301, and the arm 313 is deflected relative to the body clip interface 318 to enable it to fit inside the body 301 to permit the cap 309 to be coupled to the body 301. Next, as shown in FIG. 8C, in order to remove the cap 309 from the body 301 to place the cap 301 in an uncapped state, the cap 309 may be pulled off away from the distal end 303 along the longitudinal direction 304, in the direction of the arrow 328. This arm 313 flexes back to its unflexed/undeformed state as shown in FIG. 8D, and in this position, the blocking surface 317 of the arm bears against the body clip interface 318 to prevent the cap 309 from being re-capped, in a similar manner as shown in FIGS. 5E, 6E and 7F and described above in relation thereto.

FIGS. 9A to 9F show another example of a medicament delivery device 300, in which the cap 309 is generally similar to that shown in FIGS. 4 to 8D and described above, however the cap 309 does not comprise an arm 313. That is, in the example shown, the only feature or element protruding from the body portion 310 towards the distal end 303 of the body 301 when the cap 309 is in the orientation illustrated relative to the body 301, is the receiving portion 311. The example of FIGS. 9A to 9F further differs from the examples described above in that the medicament delivery device 300 further comprises a blocking element 321, which is separate to and not integrally formed with the cap 309, whereas in the aforementioned examples, a portion of the arm 313 may be described as functioning as a "blocking element" with the body clip interface 318. The blocking element 321 is arranged inside the body 301 and may be coupled to or integrally formed with the body 301. In the example shown, the blocking element 312 is generally wedge shaped or block shaped and comprises a chamfered surface 322 that is inclined relative to the longitudinal direction 304 and that is configured to slope inwards towards a central longitudinal axis of the body 301 in a direction from the proximal end 302 towards the distal end 303. In the example shown, the chamfered surface 322 is generally linear and straight, although it is also envisaged that the chamfered surface 322 may comprise a curved surface. In the example shown, the blocking element 312 is a single, discrete element, however it is also envisaged that the medicament delivery device 300 may alternatively comprise a plurality of blocking elements 312, which may be angularly spaced apart from one another about the circumference of an inner surface of the body 301, which may advantageously reduce off-centre bending forces. It is also envisaged that the blocking element 312 may be generally annular and may extend around the entire circumference of an inner surface of the body 301, or at least around a substantial portion thereof.

The blocking element 321 is configured to move relative to the body 301 and relative to the pre-filled syringe 306, the needle cover 307, the cap insert 308, and the cap 309, along a radial direction 325. The radial direction 325 is generally normal to the longitudinal direction 304. The blocking element 321 is configured to move along the radial direction 325 in order to selectively block or otherwise impede movement of the cap 309 along the longitudinal direction 304, in order to prevent re-capping as required. The blocking element 312 may additionally or alternatively be configured to move along the radial direction 325 in order to selectively block or otherwise impede movement of the needle cover 307 and/or the cap insert 308, which are coupled to the cap 309 once the cap 309 has been placed in the capped position, and thereafter. The blocking element 312 may thus be configured to be arranged in a first state, in which the blocking element 312 is arranged in a radially outward position, and a second state, in which the blocking element 312 is arranged in a radially inward position. The radially inward position is radially inward relative to the radially outward position, such that when the blocking element 312 is in the radially inward position it is closer to a central longitudinal axis of the body 301 than when the blocking element 312 is in the radially outward position. The blocking element 312 is configured to block movement of the cap 309 from the uncapped position into the capped position, i.e. to prevent the contact surface 312 from being brought into contact with the distal end 303, when the blocking element 321 is in the second state, i.e. when it is in the radially inward position. The blocking element 321 is biased towards the second state, i.e. towards the radially inward position, such that some kind of force or actuation is required to place it in the first state in which the cap 309 is free to be placed in the capped position. The blocking element 312 may be biased towards the second blocking state by coupling it to the body 301 by a spring 337 for example (see blocking element 321b and spring 337 in FIG. 10 for example).

Figures 9A, 9B, 9C, 9D, 9E, 9F:
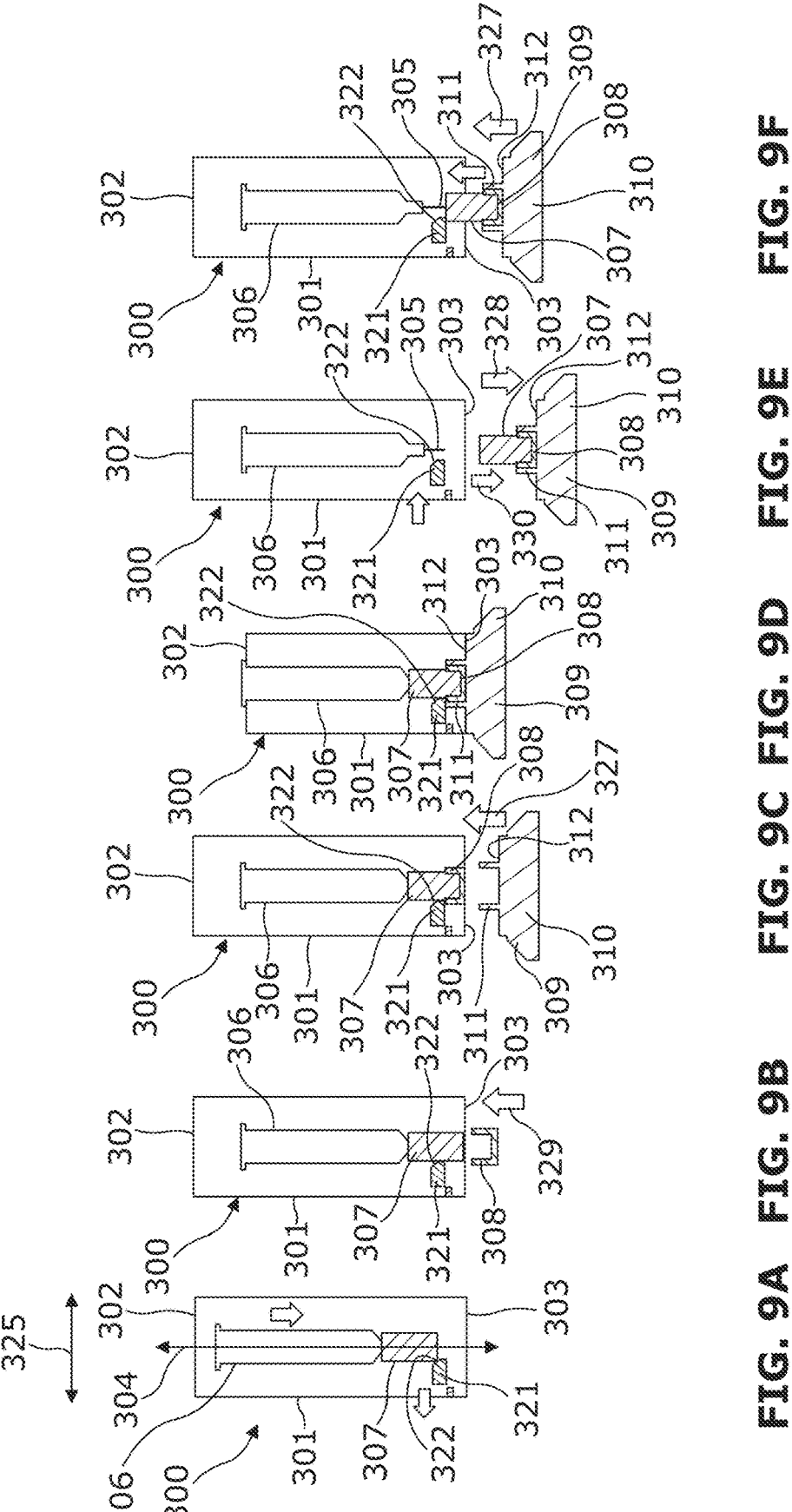
FIG. 9A shows a schematic cross-sectional view of a medicament delivery device in a pre-assembled state.
FIG. 9B shows a schematic cross-sectional view of a medicament delivery device in a pre-assembled state.
FIG. 9C shows a schematic cross-sectional view of a medicament delivery device with the cap uncapped.
FIG. 9D shows a schematic cross-sectional view of a medicament delivery device with the cap capped.
FIG. 9E shows a schematic cross-sectional view of a medicament delivery device during removal of the cap.
FIG. 9F shows a schematic cross-sectional view of a medicament delivery device with the cap uncapped.

FIG. 9A shows the blocking element 321 in the second state, in which it is in a radially inward position. The chamfered surface 322 is arranged to contact and abut with the needle cover 307, such that movement of the pre-filled syringe 306 and the needle cover 307 along the longitudinal direction 304 inside the body 301 towards the distal end 303 causes the needle cover 307 to bear against and slide relative to the chamfered surface 322, which causes the blocking element 321 to be pushed outwards, against the direction in which it is biased, for example by a biasing means such as a spring, along the radial direction 325, into the first state which is a radially outward position as shown in FIG. 9B. Next, the cap insert 308 may be fitted to the needle cover 307 by moving the cap insert 308 along the longitudinal direction 304 in the direction shown by the arrow 329. The cap insert 308 may be configured to bear against the blocking element 321, as shown in FIG. 9C, to prevent the cap insert 308 and hence also the needle cover 307 and the pre-filled syringe 306 from inadvertently being pushed along the longitudinal direction 304 towards the proximal end 302.

Next as shown in FIG. 9C, the cap 309 is fitted to the body 301 by moving the cap 309 along the longitudinal direction 304 towards the distal end 303 in the direction shown by the arrow 327, to bring the contact surface 312 into contact with the distal end 303, into the position shown in FIG. 9D. At this stage, the blocking element 321 is still in the first state in which the blocking element 312 is in a radially outward position, such that the cap 309 is unobstructed from moving along the longitudinal direction 304 to bring the contact surface 312 into contact with the distal end 303, to arrange the cap 309 in the capped position, as shown in FIG. 9E. When desired, the cap 309 may then be removed, together with the needle cover 307 and the cap insert 308, by moving the cap 309 along the longitudinal direction 304 away from the distal end 303, in the direction shown by the arrow 328 in FIG. 9E. As shown in FIG. 9E, when the cap 309 is removed, the needle cover 307 is also removed such that it is no longer inside the body 301, since the needle cover 307 is coupled to the cap 309, for example by an interference fit. Hence, once the cap 309 is removed as shown in FIG. 9E, the needle cover 307 is no longer arranged inside the body 301 to radially contact and abut the blocking element 321. Hence, the needle cover 307 no longer pushes against the blocking element 321 to apply a radially outward force thereto to counteract the biasing force, for example a spring force, which biases the blocking element 321 radially inwards towards the second state as shown in FIG. 9A. Thus, once the cap 309 and hence also the needle cover 307 are removed, the blocking element 321 is caused to move back into the second state in which it is in a radially inward position. In this state, the blocking element 321 is radially arranged such that its innermost surface is arranged to be closer to a central longitudinal axis of the body 301 than the outer radius of the needle cover 307 is relative to said central longitudinal axis. In other words, the innermost surface of the blocking element 321 is arranged to overlap with the needle cover 307, such that a lowermost or distal surface of the blocking element 321 is configured to contact and abut with an uppermost or proximal surface of the needle cover 307 when the cap 309 is in the uncapped state and the blocking element 321 is in the second radially inward state. Thus, as shown in FIG. 9F, the blocking element 321 blocks the needle cover 307 from being able to be moved further inside the body 301 along the longitudinal direction 304, towards the proximal end 302. Because the needle cover 307 is coupled to the cap 309 at this stage, this means that the cap 309 is hence obstructed by the blocking element 321 from moving further along the longitudinal direction 304 towards the distal end 303 along the direction shown by the arrow 328, such that the cap 309 is blocked from being placed into the capped position again, hence re-capping is prevented. Instead, as shown in FIG. 9F, the longitudinal movement of the cap 309 is limited such that the receiving portion 311 and the contact surface 312 are spaced apart from the distal end 303 of the body at the maximum possible longitudinal displacement of the cap 309.

In the example shown in FIGS. 9A to 9F, in which the blocking element 321 is an element which is movable relative to the body 301, the needle cover 307, the cap insert 308 and the cap 309, said movement is configured to be generally linear and translational along the radial direction 325 as described above, and the blocking element 321 is generally block shaped or wedge shaped. It is also envisaged that the blocking element 321, or a plurality of blocking elements 321, may each have any other suitable form. For example, in the example of FIGS. 10A to 10F, the blocking element 321 is in the form of a leg which has a fixed end 323 coupled to or integrally formed with the body 301, and a free end 324 opposite to the fixed end 323. The free end 324 is configured to be movable relative to the fixed end 323, for example by the leg blocking element 321 being flexible, deflectable or otherwise deformable. In this manner, the leg blocking element 321 can be moved between a first state in which the free end 324 is in a radially outward position such that the leg blocking element 321 does not obstruct longitudinal movement of the needle cover 307, and a second state in which the free end 324 is in a radially inward position such that the leg blocking element 321 does obstruct longitudinal movement of the needle cover 307 to prevent re-capping of the cap 309, in a similar manner to as described above in relation to the examples of FIGS. 9A to 9F. The blocking element 321 of FIGS. 10A to 10F differs from the blocking element 321 of FIGS. 9A to 9F in that rather than the blocking element 321 being a block or wedge shape that is moved between the first state/radially outward position and the second state/radially inward position by a linear translational movement along the radial direction 325, instead the fixed end 323 of the blocking element 321 is configured to remain stationary relative to the body 301, whilst the free end 324 is configured to be movable relative to the fixed end 323 and the body 301. In the example shown, this is achieved by the flexibility, deflectability or deformability of the leg 321, and the leg blocking element 321 is biased towards the radially inward position (the second state), by means of the leg blocking element 321 being flexed/deflected/deformed when it is in the radially outward position (the first state), as described below.

Figures 10A, 10B, 10C, 10D, 10E, 10F, 11:
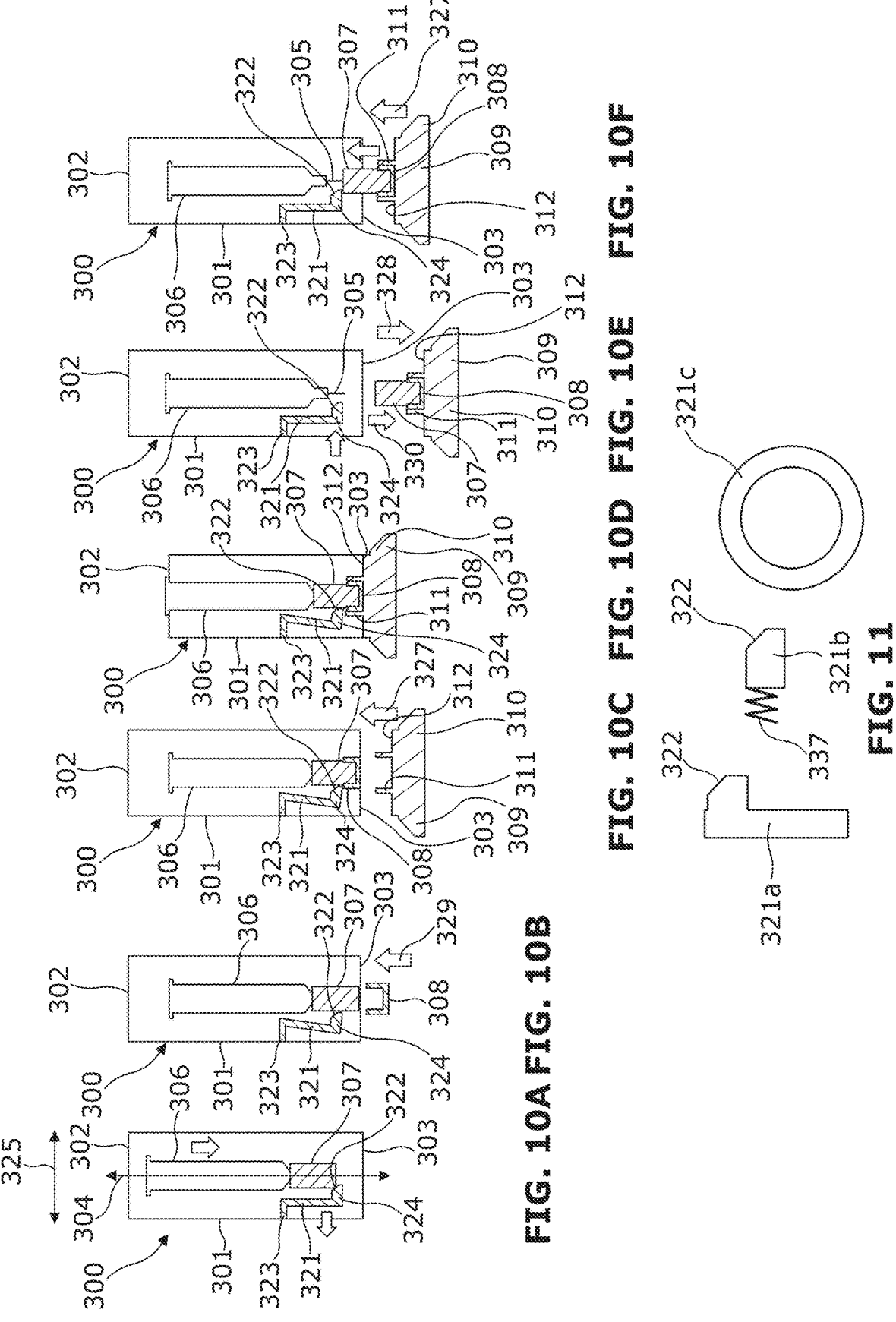
FIG. 10A shows a schematic cross-sectional view of a medicament delivery device in a pre-assembled state.
FIG. 10B shows a schematic cross-sectional view of a medicament delivery device; in a pre-assembled state.
FIG. 10C shows a schematic cross-sectional view of a medicament delivery device with the cap uncapped.
FIG. 10D shows a schematic cross-sectional view of a medicament delivery device with the cap capped.
FIG. 10E shows a schematic cross-sectional view of a medicament delivery device during removal of the cap.
FIG. 10F shows a schematic cross-sectional view of a medicament delivery device with the cap uncapped.
FIG. 11 shows three exemplary blocking elements for a medicament delivery device.

FIG. 10A shows the medicament delivery device 300 with the cap 309 not yet assembled. The leg blocking element 321 is in a natural, unbiased state, such that the free end 324 of the leg blocking element 321 is in the second state such that it is in a radially inward position. A main portion of the leg blocking element 321 which extends between the fixed end 323 and the free end 324 is arranged to be generally parallel to the longitudinal direction 304 when the leg blocking element 321 is in this state. A chamfered surface 222 is arranged at the free end 324 of the leg blocking element 321 and is inclined relative to the longitudinal direction 204, in a similar manner to the chamfered surface 222 described above in relation to the example of FIGS. 9A to 9F. The chamfered surface 222 is configured to bear against the needle cover 307 and facilitates relative movement between the needle cover 307 and the leg blocking element 321, and facilitates flexing of the leg blocking element 321 to permit the free end 324 to move between the radially inward and radially outward positions.

FIG. 10B shows the medicament delivery device 300 in a pre-use state in which the pre-filled syringe 306 and the needle cover 307 have been displaced inside and relative to the body 301 along the longitudinal direction 304 towards the distal end 303. In doing so, movement of the needle cover 307 towards the distal end 303 causes the needle cover 307 to slide against the chamfered surface 322 and force the leg bocking element 321 to deflect, into the position shown in FIG. 10B, in a similar manner to how distal movement of the needle cover 307 interacts with the chamfered surface 322 in the example shown in FIGS. 9A and 9B which forces the block shaped blocking element 321 to move radially outwards. When the leg blocking element 321 is in the position shown in FIG. 10B, the main portion of the leg blocking element 321 which connects the fixed end 323 and the free end 324 is no longer arranged to be generally parallel to the longitudinal direction 304 as shown in FIG. 10A, but is instead flexed, deflected or otherwise deformed, such that it is angled relative to the longitudinal direction 304. Thus, the free end 324 is arranged to be radially closer to the fixed end 323 than in the position shown in FIG. 10A, hence the free end 324 is arranged to be radially outward, and further away from a central longitudinal axis of the body 301. The needle cover 307 pushes against the leg blocking element 321 to counteract the force which biases it into the undeflected position shown in FIG. 10A. Once the needle cover 307 is in the position shown in FIG. 10B, the cap insert 308 may be fitted to the needle cover 307 by moving it along the longitudinal direction 304 towards the distal end 303 along the direction shown by the arrow 329.

Next, as shown in FIG. 10C, the cap 309 may be coupled to the cap insert 308 by moving the cap 309 along the longitudinal direction 304 towards the distal end 303 along the direction shown by the arrow 327. At this stage, the leg blocking element 213 is in the deflected position such that the free end 324 is arranged in the first radially outward state, hence the cap 309 is unobstructed from being placed in the capped position, so the contact surface 213 can be brought into contact with to abut the distal end 303 of the body 301, into the position shown in FIG. 10D. When desired, the cap 309 may then be removed by moving it away from the distal end 303 of the body 301 along the longitudinal direction 304 in the direction of the arrow 328, which thus also causes the needle cover 307 and the cap insert 308 to move out from inside the body 301 and away from the distal end 303 along the direction shown by the arrow 330. Hence, once the cap 309 is removed, together with the cap insert 308 and needle cover 307 to which it is coupled, the needle cover 307 is pulled out from the body 301 such that it no longer obstructs the free end 324 of the leg blocking element 321, so that the leg blocking element 321 is caused to unflex, undeflect or otherwise undeform, to go back into its natural straight state in which the afore-mentioned main portion is arranged to be generally parallel to the longitudinal direction 304, as shown in FIG. 10E. In this undeflected state, the free end 324 of the leg blocking element 321 is arranged in the second radially inward state in which it is arranged closer to the central longitudinal axis 304. In this position, due to the relative sizes and shapes thereof, for example similarly as described above in relation to FIGS. 9A to 9F, the free end 324 is arranged to radially overlap with the needle cover 307 such that as shown in FIG. 10F, the leg blocking element 321 serves to limit the range of longitudinal movement of the needle cover 307 into the body 301 along the direction shown by the arrow 307. Hence the range of longitudinal movement of the cap 309 along the direction shown by the arrow 327 is also limited, such that when the needle cover 307 abuts the free end 324 of the leg blocking element 321, the cap 309 cannot get any closer to the distal end 303 than the position shown in FIG. 10F, hence the cap 309 is prevented from being re-capped.

The examples of FIGS. 9A to 10F commonly comprise a blocking element 321 coupled to or integrally formed with the body 301 and of which at least a portion is configured to move in a radial direction 325 that is generally normal to the longitudinal direction 304, such that when the blocking element 321 is in a first state, said at least a portion of the blocking element 321 is arranged in a radially outward position and movement of the cap 309 from the uncapped position into the capped position is permitted, and such that when the blocking element 321 is in a second state, said at least a portion of the blocking element 321 is arranged in a radially inward position that is radially inward relative to the radially outward position, and movement of the cap 309 from the uncapped position into the capped position is prevented. Such radial movement may be achieved, for example, by a linear translational movement as in the example of FIGS. 9A to 9F, and/or by a pivoting or deflect-ing/flexing movement as in the example of FIGS. 10A to 10F. It is also envisaged that such radial movement may be achieved in any other suitable way, and that said movement need not necessarily be in the radial direction 325, but may for example be in the longitudinal direction 304 or any other suitable direction or range of motion to serve to selectively block the motion of the cap 309 from the uncapped position to the capped position.

It is also envisaged that the blocking element 321 need not necessarily be in the form of a block or wedge shape as in the example of FIGS. 9A to 9F, or in the form of a leg shape as in the example of FIGS. 10A to 10F, and that the blocking element 321 may have any other suitable shape or form. Some examples of blocking element are shown in FIG. 11. The blocking element 321 may comprise a flexible arm 321a comprising a chamfered surface 322, a wedge or block shape 321b comprising a chamfered surface 322 and coupled to the body 301 via a spring 337, or an annulus or ring 321c. The annular ring shaped blocking element 321c may be oriented to be generally normal to the longitudinal direction 304 such that it circumscribes a central longitudinal axis of the body 201. The ring 321c may be configured to selectively become larger and smaller in diameter, for example by being formed of a stretchable or elastic material, or by being configured to be stretchable by means of its geometry, for example by comprising one or more folds or similar elements, in order to provide for the aforementioned feature of at least a portion of the ring 321c being movable along the radial direction 325 to provide said radially inward and radially outward positions, to selectively block movement of the cap 309 from the uncapped position to the capped position when required.

Figure 12:
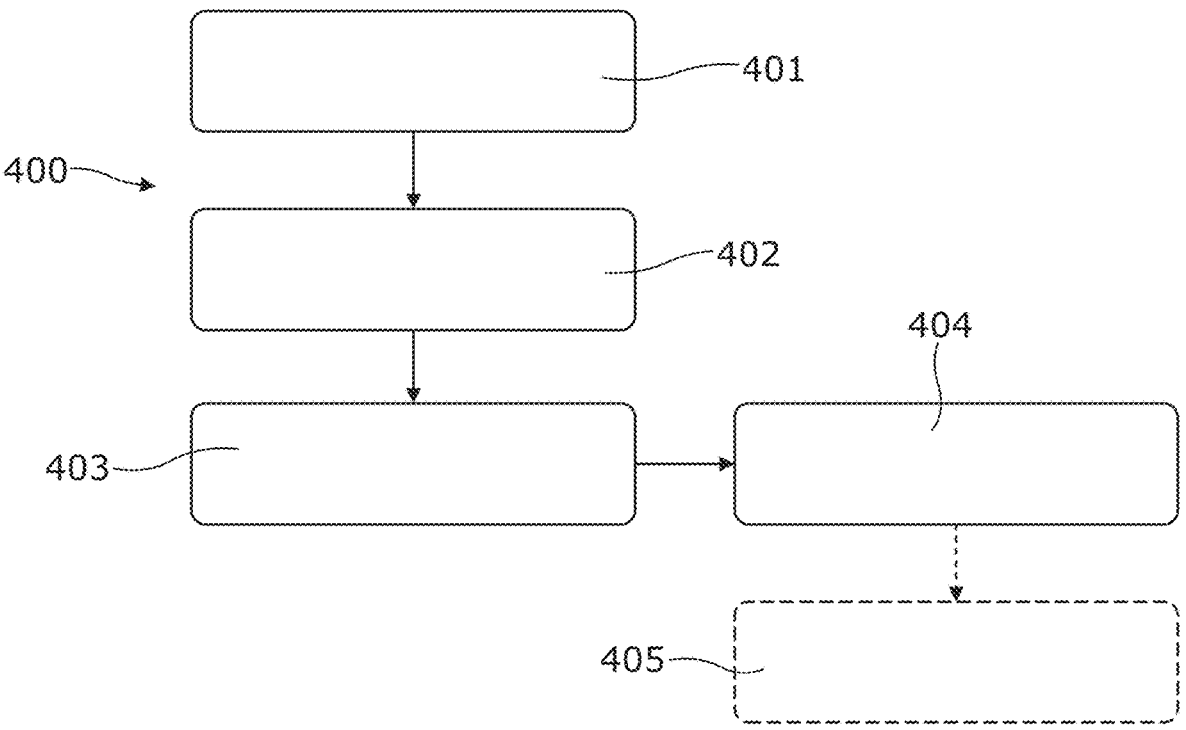
FIG. 12 shows a flowchart illustrating the steps of a method of capping a medicament delivery device, removing the cap, and then attempting to re-cap the cap.

FIG. 12 shows a flowchart illustrating the steps of a method 400 of capping the medicament delivery device 300, removing the cap, with an intention to use the medicament delivery device 300 to deliver medicament from the needle 305, and then attempting to re-cap the delivery device 300, regardless of whether said medicament has been delivered. In said method, as in the examples described above, the cap is blocked or otherwise prevented from being re-capped, to avoid or at least reduce the risk of the needle 305 bending, thus avoiding the aforementioned risks associated therewith. In step 401, the medicament delivery device 300 is in a pre-assembled state and the cap insert 308 is fitted to the needle cover 307, to prepare for the cap 309 to be fitted. In step 402, the cap 309 is fitted to the cap insert 308 to couple it thereto. With an intention to use the medicament delivery device 300 or the delivery of medicament via the needle 305, the user may then remove the cap 309 in step 403. Depend-ing on the configuration of the medicament delivery device 300, the occurrence of steps 402 and/or 403 cause step 404 to occur, which comprises the blocking element 321 being caused to be arranged in a second state in which movement of the cap 309 from the uncapped position into the capped position is prevented, whereas in step 402 when the cap 309 was fitted to the cap insert 308, the blocking element 321 may have been arranged in a first state in which movement of the cap 309 from the uncapped position into the uncapped position was permitted. After step 404, in case a user tries to attempt, in a step 405, to re-cap the cap 309 back onto the body 301, this is not possible because the blocking element 321 obstructs this, such as in the examples described above.

From the above exemplary medicament delivery devices 300 and the associated descriptions of their operation, it is to be understood that whilst the cap 309 is arrangeable in a capped position and an uncapped position, a blocking ele-ment serves to selectively block movement of the cap 309 from the uncapped position into the capped position, such that the blocking element may be arranged to permit a first movement of the cap 309 from the uncapped position into the capped position, to allow the medicament delivery device 300 to be capped initially, to assemble it ready for use, but that the blocking element may also be arranged to, when required, block movement of the cap 309 back into the capped position from the uncapped position, i.e. once the cap 309 has already previously been capped, in order to prevent recapping. The blocking element is thus arrangeable in a first state in which movement of the cap 309 from the uncapped position into the capped position is permitted, to permit initial capping of the cap 309 to assembly the medicament delivery device 300, and a second state in which movement of the cap 309 from the uncapped position into the capped position is prevented, to prevent re-capping, i.e. to prevent subsequent capping. Moving the cap 309 from an initial capped position (e.g. an initial capped position) into the uncapped position (i.e. removing the cap 309 to place the medicament delivery device 300 in a ready to use state), or moving the cap from the uncapped position into an initial capped position, or both moving the cap from the uncapped position into the capped position and then back into the uncapped position again, causes the blocking element to be arranged in the second state. It is to be understood by the aforementioned examples and the associated drawings that the "blocking element" may comprise part of the cap 309 (for example as in FIGS. 5A to 5E), or an element that is external from the cap 309 and which may for example be integrally formed with or coupled to the body 301 (as in FIGS. 10A to 10F for example). It is also envisaged that the "blocking element" may comprise both a part of the cap 309 and a part external to the cap, said parts being configured to cooperate with one another to provide the aforementioned selective blocking function. It is also to be understood from the above examples that in order to provide said first and second states of the blocking element, the cap 309 may be moved relative to the body 301 and/or relative to a blocking element that is integrally formed with or coupled to the body 301; or that the body 301 and/or a blocking element that is integrally formed with or coupled to the body 301 may be moved relative to the cap 309; or that both the cap 309 and the body and/or a blocking element that is integrally formed with or coupled to the body 301 may be together moved relative to one another, either simultaneously or sequentially. Said movement may for example be a longitudinal movement, a rotational movement, or both a longitudinal and a rotational movement which may occur simultaneously or sequentially.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, small modular immunopharmaceuticals (SMIP), binding-domain immunoglobulin fusion proteins, camelized antibodies, and immunoglobulin single variable domains. Additional examples of antigen-binding antibody fragments are known in the art.

The term "immunoglobulin single variable domain" (ISV), interchangeably used with "single variable domain", defines immunoglobulin molecules wherein the antigen binding site is present on, and formed by, a single immunoglobulin domain. As such, immunoglobulin single variable domains are capable of specifically binding to an epitope of the antigen without pairing with an additional immunoglobulin variable domain. The binding site of an immunoglobulin single variable domain is formed by a single heavy chain variable domain (VH domain or VHH domain) or a single light chain variable domain (VL domain). Hence, the antigen binding site of an immunoglobulin single variable domain is formed by no more than three CDRs.

An immunoglobulin single variable domain (ISV) can be a heavy chain ISV, such as a VH (derived from a conventional four-chain antibody), or VHH (derived from a heavy-chain antibody), including a camelized VH or humanized VHH. For example, the immunoglobulin single variable domain may be a (single) domain antibody, a "dAb" or dAb or a Nanobody® ISV (such as a VHH, including a humanized VHH or camelized VH) or a suitable fragment thereof. [Note: Nanobody® is a registered trademark of Ablynx N.V.]; other single variable domains, or any suitable fragment of any one thereof.

"VHH domains", also known as VHHs, VHH antibody fragments, and VHH antibodies, have originally been described as the antigen binding immunoglobulin variable domain of "heavy chain antibodies" (i.e., of "antibodies devoid of light chains"; Hamers-Casterman et al. 1993 (Nature 363:446-448). The term "VHH domain" has been chosen in order to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). For a further description of VHH's, reference is made to the review article by Muyldermans 2001 (Reviews in Molecular Biotechnology 74:277-302).

For the term "dAb's" and "domain antibody", reference is for example made to Ward et al. 1989 (Nature 341:544), to Holt et al. 2003 (Trends Biotechnol. 21:484); as well as to WO 2004/068820, WO 2006/030220, WO 2006/003388. It should also be noted that, although less preferred in the context of the present invention because they are not of mammalian origin, single variable domains can be derived from certain species of shark (for example, the so-called "IgNAR domains", see for example WO 2005/18629).

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

An example of a compound to be administered with the drug delivery device disclosed herein is a compound with the INN tirzepatide, as referenced in claim 1 of U.S. Pat. No. 9,474,780.

An example of a pharmaceutical composition to be administered with the drug delivery device disclosed herein is a pharmaceutical composition as referenced in U.S. Pat. No. 11,357,820.

An example of a pharmaceutical composition to be administered with the drug delivery device disclosed herein includes a 0.5 mL solution of 2.5 mg, 5 mg, 7.5 mg, 10 mg, 12.5 mg, or 15 mg of tirzepatide and the following excipients sodium chloride (4.1 mg), sodium phosphate dibasic heptahydrate (0.7 mg), and water for injection. Hydrochloric acid solution and/or sodium hydroxide solution may be added to adjust the pH.

An example starting dosage tirzepatide may be 2.5 mg injected subcutaneously once weekly. After four weeks, the tirzepatide dosage may be increased to 5 mg injected subcutaneously once weekly. The dosage may be further increased in 2.5 mg increments after at least four weeks on the current dose. In an example, the maximum dosage of tirzepatide may be 15 mg injected subcutaneously once weekly. If a dose is missed, patients may be instructed to administer tirzepatide as soon as possible within four days (96 hours) after the missed dose. If more than four days have passed, patients may skip the missed dose and administer the next dose on the regularly scheduled day. In each case, patients may then resume their regular once weekly dosing schedule. The day of weekly administration may be changed, if necessary. The time between two doses may be at least three days (72 hours).

Tirzepatide dosages may include 2.5 mg/0.5 mL, 5 mg/0.5 mL, 7.5 mg/0.5 mL, 10 mg/0.5 mL, 12.5 mg/0.5 mL, and 15 mg/0.5 mL. Tirzepatide may be stored in a refrigerator at 2° C. to 8° C. (36° F. to 46° F.). A single-dose pen or single-dose vial may be stored unrefrigerated at temperatures not to exceed 30° C. (86° F.) for up to 21 days. Tirzepatide may be stored in a carton.

Those of skill in the art will understand that modifications (additions and/or removals) of various components of the embodiments described herein may be made without departing from the full scope and spirit of the present invention, which encompass such modifications and any and all equivalents thereof.

LIST OF REFERENCE NUMBERS

10—device
11—housing

12—cap
13—needle sleeve
17—needle
20—distal region
21—proximal region
22—button
23—piston
200—medicament delivery device
201—body
202—distal end of the body
208—locking member
216—lock ring
217—needle
223—plunger
227—actuation member
228—button
229—dispensing mechanism
232—injection site
240—spring guide
242—protrusions
250—syringe
254—cap
258—stop
260—spring
262—spring
264—clip
265—proximal opening
266—needle shield
267—collar
268—collar
300—medicament delivery device
301—body
302—proximal end
303—distal end
304—longitudinal direction
305—needle
306—pre-filled syringe
307—needle cover
308—cap insert
309—cap
310—body portion
311—receiving portion
312—contact surface
313—arm
314—free end
315—fixed end
316—chamfered surface
317—blocking surface
318—body clip interface
319—chamfered surface
321—blocking element
321*a*—blocking element
321*b*—blocking element
321*c*—blocking element
322—chamfered surface
323—fixed end
324—free end
325—radial direction
326—downward force direction
327—direction of movement
328—direction of movement
329—direction of movement
330—direction of movement
332—direction of rotational movement
333—direction of rotational movement
334—assembly fixture
335—outermost surface

336—innermost surface
337—spring
400—method
401—method step
402—method step
403—method step
404—method step
405—method step

The invention claimed is:

1. A medicament delivery device, comprising:
a body having a proximal end and a distal end defining a longitudinal direction;
a needle for injecting medicament into a user and configured to be arranged in an injecting position in which the needle protrudes from the distal end of the body;
a needle shield assembly receivable inside the body and comprising (i) a needle cover configured to circumscribe at least a portion of the needle, and (ii) a cap insert configured to receive the needle cover;
a cap moveable along the longitudinal direction and arrangeable in a capped position in which the cap conceals the distal end of the body, a first initial uncapped position in which the cap has not previously been in the capped position, and a second subsequent uncapped position in which the cap has previously been in the capped position, wherein when the cap is in the first initial uncapped position and the second subsequent uncapped position, at least a portion of the cap is spaced apart from the distal end of the body; and
a blocking element, wherein when the cap is in the first initial uncapped position, the needle cover inside the body is configured to position the blocking element in a first state in which movement of the cap from the first initial uncapped position into the capped position is permitted, and wherein when the cap is moved from the capped position into the second subsequent uncapped position, the cap is configured to receive the cap insert such that the needle shield assembly is coupled to the cap and removed from the body, causing the blocking element to be arranged in a second state in which movement of the cap from the second subsequent uncapped position into the capped position is prevented.

2. The medicament delivery device of claim 1, wherein when the cap is in the capped position, the cap is coupled to the body, and when the cap is in the first initial uncapped position and the second subsequent uncapped position, the cap is decoupled from the body.

3. The medicament delivery device of claim 1, wherein the cap is configured to move from the first initial uncapped position in which the cap has not previously been in the capped position, into the capped position, to cause the cap to be coupled to the needle shield assembly.

4. The medicament delivery device of claim 1, wherein the needle shield assembly is configured to be movable relative to the body along the longitudinal direction, such that when the needle shield assembly is coupled to the cap, the needle shield assembly and the cap are configured to be movable together relative to the body along the longitudinal direction.

5. The medicament delivery device of claim 1, wherein when the cap is in the first initial uncapped position and the needle shield assembly is not coupled to the cap, the blocking element is configured to be in the first state; and wherein when the cap is in the second subsequent uncapped position and the needle shield assembly is coupled to the cap, the blocking element is configured to be in the second state.

6. The medicament delivery device of claim 1, wherein when the cap is in the capped position, the cap is configured to form a snap fit connection with the body to couple the cap to the body.

7. The medicament delivery device of claim 6, wherein moving the cap from the first initial uncapped position in which the cap has not previously been in the capped position, into the capped position, is configured to cause the cap and the body to be arranged in the snap fit connection.

8. The medicament delivery device of claim 1, wherein the blocking element comprises a chamfered surface inclined relative to the longitudinal direction.

9. The medicament delivery device of claim 1, wherein the blocking element is coupled to or integrally formed with the body and wherein at least a portion of the blocking element is configured to move in a radial direction that is generally normal to the longitudinal direction, such that when the blocking element is in the first state, said at least a portion of the blocking element is arranged in a radially outward position, and such that when the blocking element is in the second state, said at least a portion of the blocking element is arranged in a radially inward position that is radially inward relative to the radially outward position, relative to a central longitudinal axis of the medicament delivery device; and wherein the blocking element is biased towards the radially inward position.

10. The medicament delivery device of claim 1, wherein the medicament delivery device contains the medicament.

\* \* \* \* \*